(12) United States Patent
Zarling et al.

(10) Patent No.: US 6,255,113 B1
(45) Date of Patent: *Jul. 3, 2001

(54) HOMOLOGOUS SEQUENCE TARGETING IN EUKARYOTIC CELLS

(75) Inventors: David A. Zarling, Menlo Park; Elissa P. Sena, Palo Alto, both of CA (US)

(73) Assignee: SRI International, Menlo Park, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/385,713

(22) Filed: Feb. 8, 1995

Related U.S. Application Data

(63) Continuation of application No. 07/939,767, filed on Sep. 2, 1992, now abandoned, which is a continuation-in-part of application No. 07/873,438, filed on Apr. 24, 1992, now abandoned.

(51) Int. Cl.$^7$ .......................... C12N 15/63; C12N 15/00; C12N 15/09; C12N 5/00

(52) U.S. Cl. .................. 435/463; 435/462; 435/455; 435/461; 435/458; 435/465; 435/320.1; 435/325; 800/25; 514/44; 424/93.21

(58) Field of Search ................ 435/172.1, 172.3, 435/320.1, 240.1, 240.2, 240.21, 463, 462, 455, 461, 458, 465, 325; 514/44; 424/93.21; 800/25

(56) References Cited

U.S. PATENT DOCUMENTS

| 4,873,191 | 10/1989 | Wagner et al. ............... 435/172.3 |
| 4,888,274 | 12/1989 | Radding et al. ............... 435/6 |
| 4,950,599 | * 8/1990 | Bertling ............... 435/172.3 |

FOREIGN PATENT DOCUMENTS

| 91/19796 | 12/1991 | (WO) . |
| 92/08791 | 5/1992 | (WO) . |
| 92/15694 | 9/1992 | (WO) . |
| 96/03736 | 3/1993 | (WO) . |
| 94/04032 | 3/1994 | (WO) . |

OTHER PUBLICATIONS

Thomas et al., 1986. Cell:44:419–428.*
Smithies et al., 1985. Nature 317:230–234.*
Hasty et al., 1991. Nature 350:243–246.*
Wu et al., 1989. The Journal of Biological Chemistry, 264(29):16985–16987.*
Orkin et al., "Report and recommedations of the Panel to Assess the NIH Investment in Research on Gene Therapy", National Institute of Health, Dec. 7, 1995.*
Felgner et al. "Lipofection: A Highly Efficient, Lipid–Mediated DNA–Transfection Procedure," *Proc. Natl. Acad. Sci. USA*, 84:7413–7417 (1987).
Drumm et al., "Correction of the Cystic Fibrosis Defect In Vitro by Retrovirus–Mediated Gene Transfer," *Cell*, 62:1227–1233 (1990).
Fields and Jang, "Presence of a Potent Transcription Activating Sequence in the p53 Protein," *Science*, 249:1046–1049 (1990).
Valancius and Smithies, "Testing and "In–Out" Targeting Procedure for Making Subtle Genomic Modifications in Mouse Embryonic Stem Cells," *Molecular and Cellular Biology*, 11(3):1402–1408 (1991).
Cox et al., "Enzymes of General Recombination," *Ann. Rev. Biochem*, 56:229–262 (1987).
Sauer and Henderson, "Targeted Insertion of Exogenous DNA into the Eukaryotic Genome by the Cre Recombinase," *New Biologist*, 2:441–449 (1990).
Dunderdale et al., "Formation and Resolution of Recombination Intermediates by *E. Coli* RecA and RuvC Proteins," *Nature*, 354(19):506–510 (1991).
Cheng et al., "RecA–Directed Hybridization of Psoralen–Monoadducted DNA Oligonucleotides to Duplex Targets," *NATO ASI Ser., Ser C., Photochemical Probes in Biochemistry*, 272:169–177, P.E. Nielsen (ed.), (1989).
Langer et al., "Enzymatic Synthesis of Biotin–Labeled Polynucleotides: Novel Nucleic Acid Affinity Probes," *Proc. Natl. Acad. Sci. USA*, 78(11):6633–6637 (1981).

(List continued on next page.)

*Primary Examiner*—Jasemine Chambers
*Assistant Examiner*—Jill D. Martin
(74) *Attorney, Agent, or Firm*—Flehr Hohbach Test Albritton & Herbert LLP; Richard F. Trecartin, Esq.

(57) ABSTRACT

The invention relates to methods for targeting an exogenous polynucleotide or exogenous complementary polynucleotide pair to a predetermined endogenous DNA target sequence in a eukaryotic cell by homologous pairing, particularly for altering an endogenous DNA sequence, such as a chromosomal DNA sequence, typically by targeted homologous recombination. In certain embodiments, the invention relates to methods for targeting an exogenous polynucleotide having a linked chemical substituent to a predetermined endogenous DNA sequence in a metabolically active eukaryotic cell, generating a DNA sequence-specific targeting of one or more chemical substituents in an intact nucleus of a metabolically active eukaryotic cell, generally for purposes of altering a predetermined endogenous DNA sequence in the cell. The invention also relates to compositions that contain exogenous targeting polynucleotides, complementary pairs of exogenous targeting polynucleotides, chemical substituents of such polynucleotides, and recombinase proteins used in the methods of the invention.

20 Claims, 10 Drawing Sheets

OTHER PUBLICATIONS

Hunger–Bertling, K., et al., "Short DNA fragments induce site specific recombination in mammalian cells", *Mol. and Cellular Biochem.*, 92:107–116 (1990).

Bertling, "Transfection of a DNA/Protein Complex into Nuclei of Mammalian Cells Using Polyoma Capsids and Electroporation," *Bioscience Reports*, 7:107–111 (1987).

Ausubel et al., "Short Protocols in Molecular Biology," 2nd ed. (John Wiley & Sons: New York), pp. 9–14 and 9–15 (1992).

Meyer Jr., R.B., et al., "Efficient, Specific Cross–Linking and Cleavage of DNA by Stable, Synthetic Complementary Oligodieoxynucleotides", *J. of the Amer. Chem. Soc.*, 111(22):8517–8519 (1989).

Kido, M., et al., "*Escherichia coli* RecA Protein Modified with a Nuclear Location Signal Binds to Chromosomes in Living Mammalian Cells", *Exper. Cell Res.*, 198:107–114 (1992).

* cited by examiner

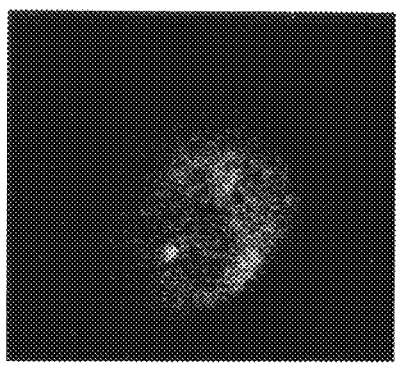
FIG._1A
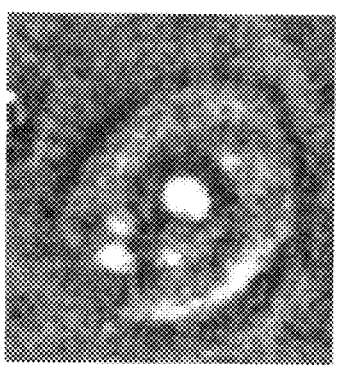
FIG._1B
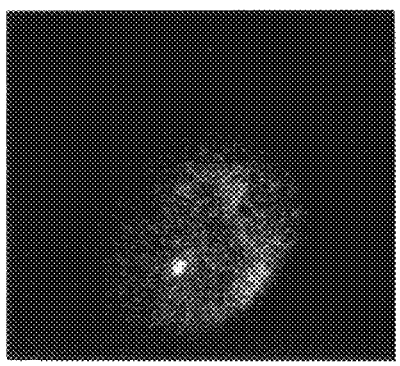
FIG._1C
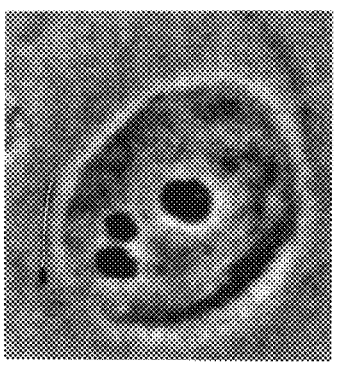
FIG._1D

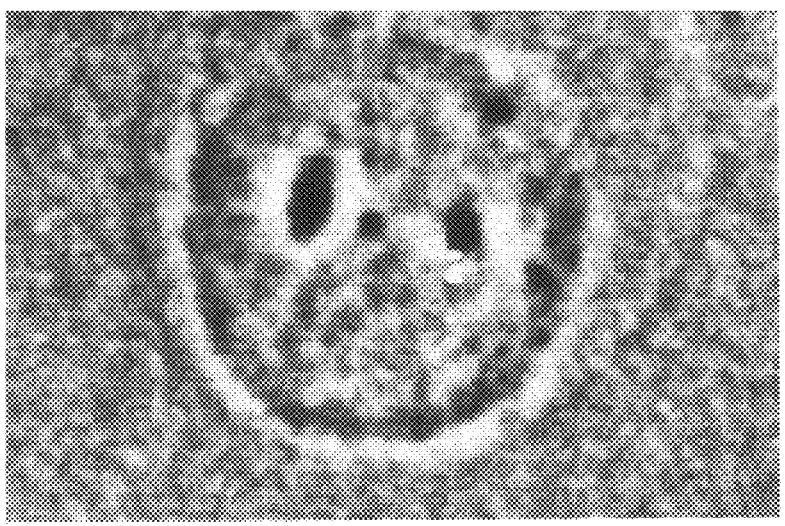
FIG._2A
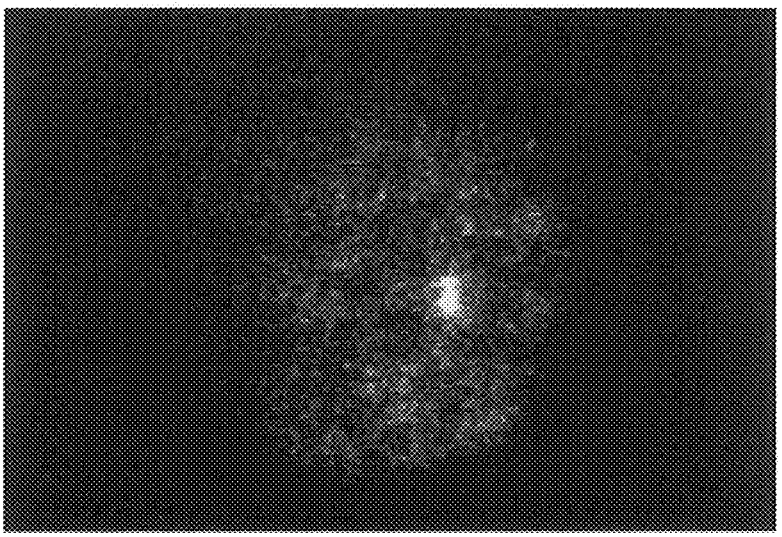
FIG._2B
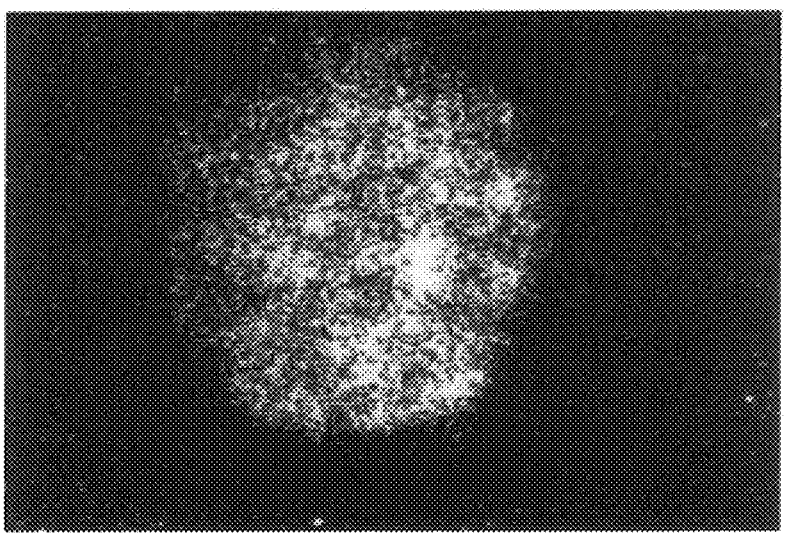
FIG._2C

FIG._3A
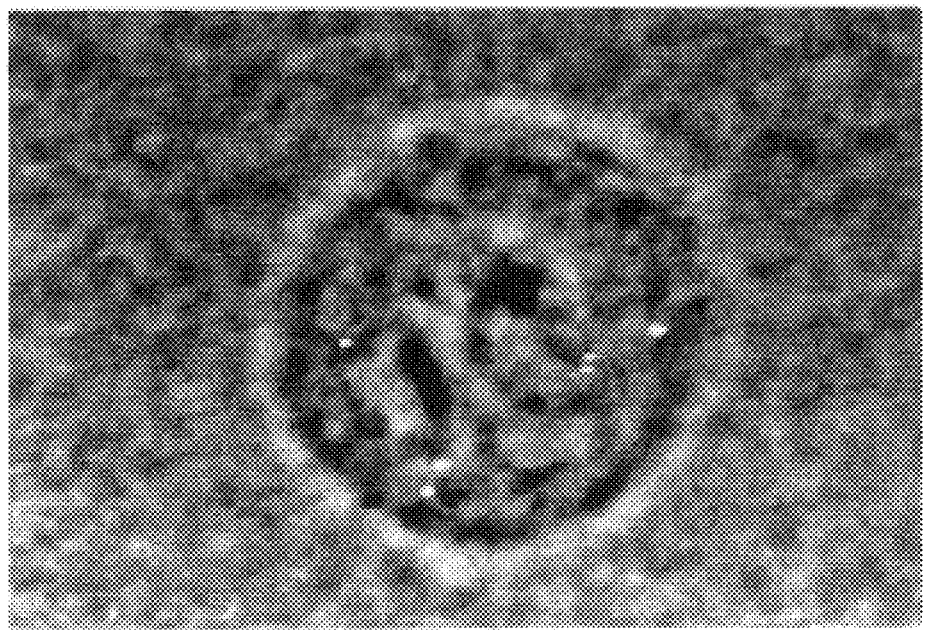
FIG._3B

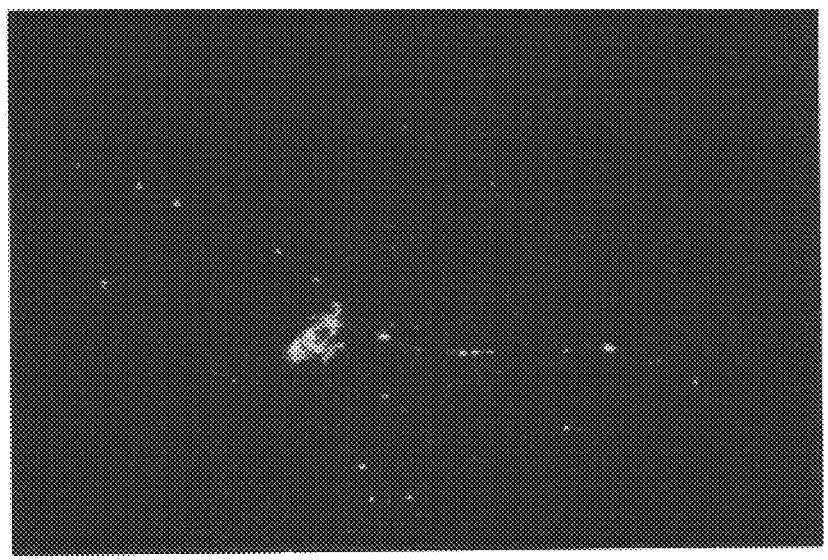
FIG._4
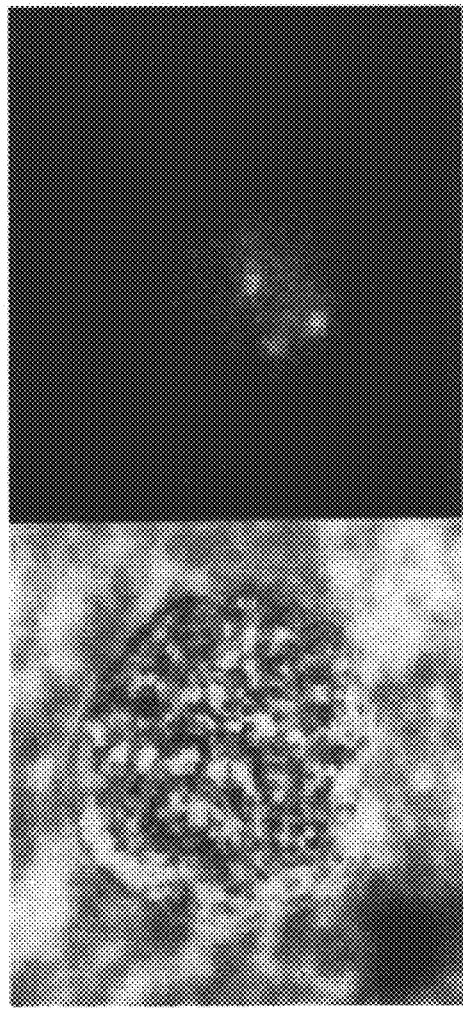
FIG._5A
FIG._5B

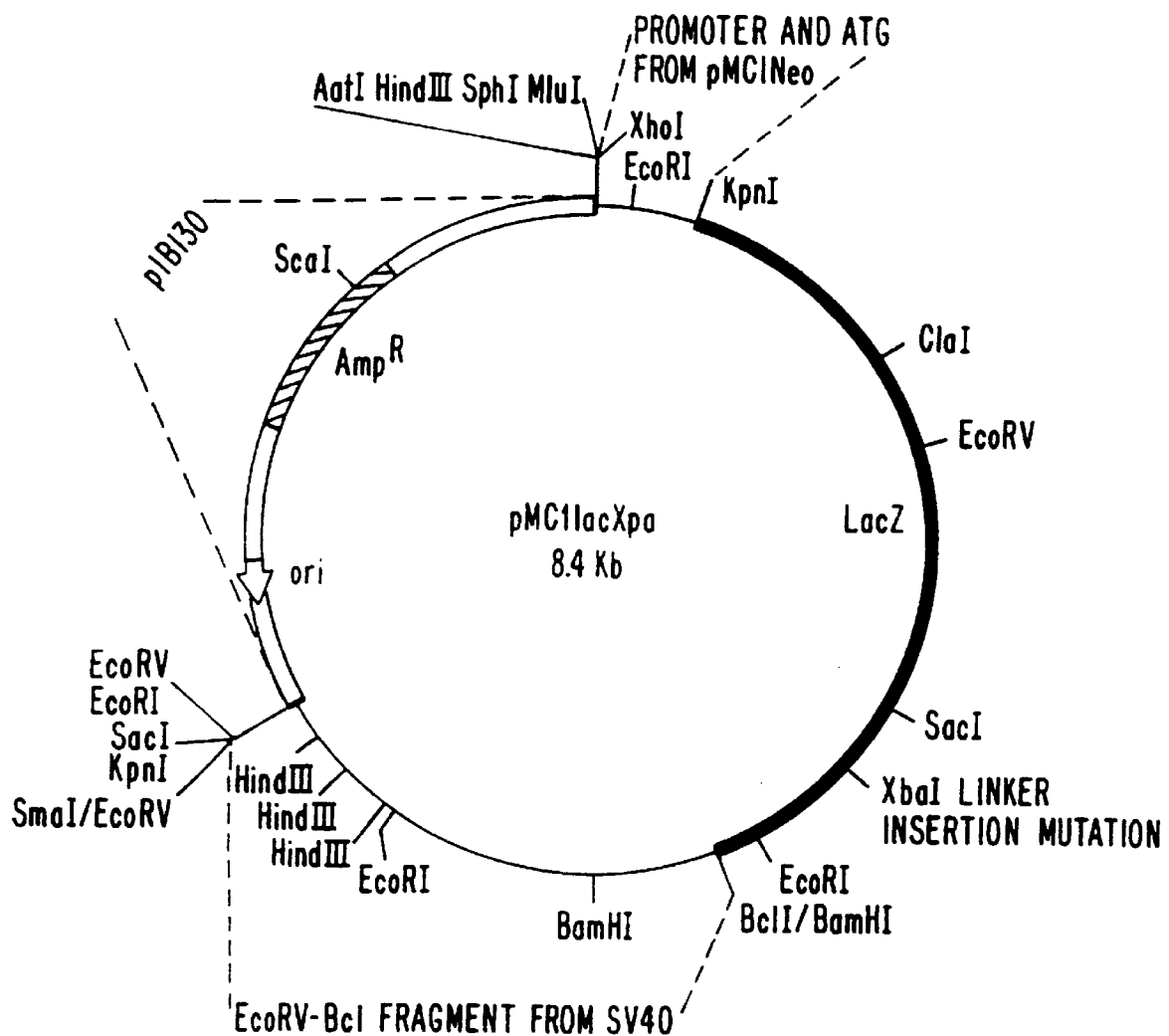
FIG._6

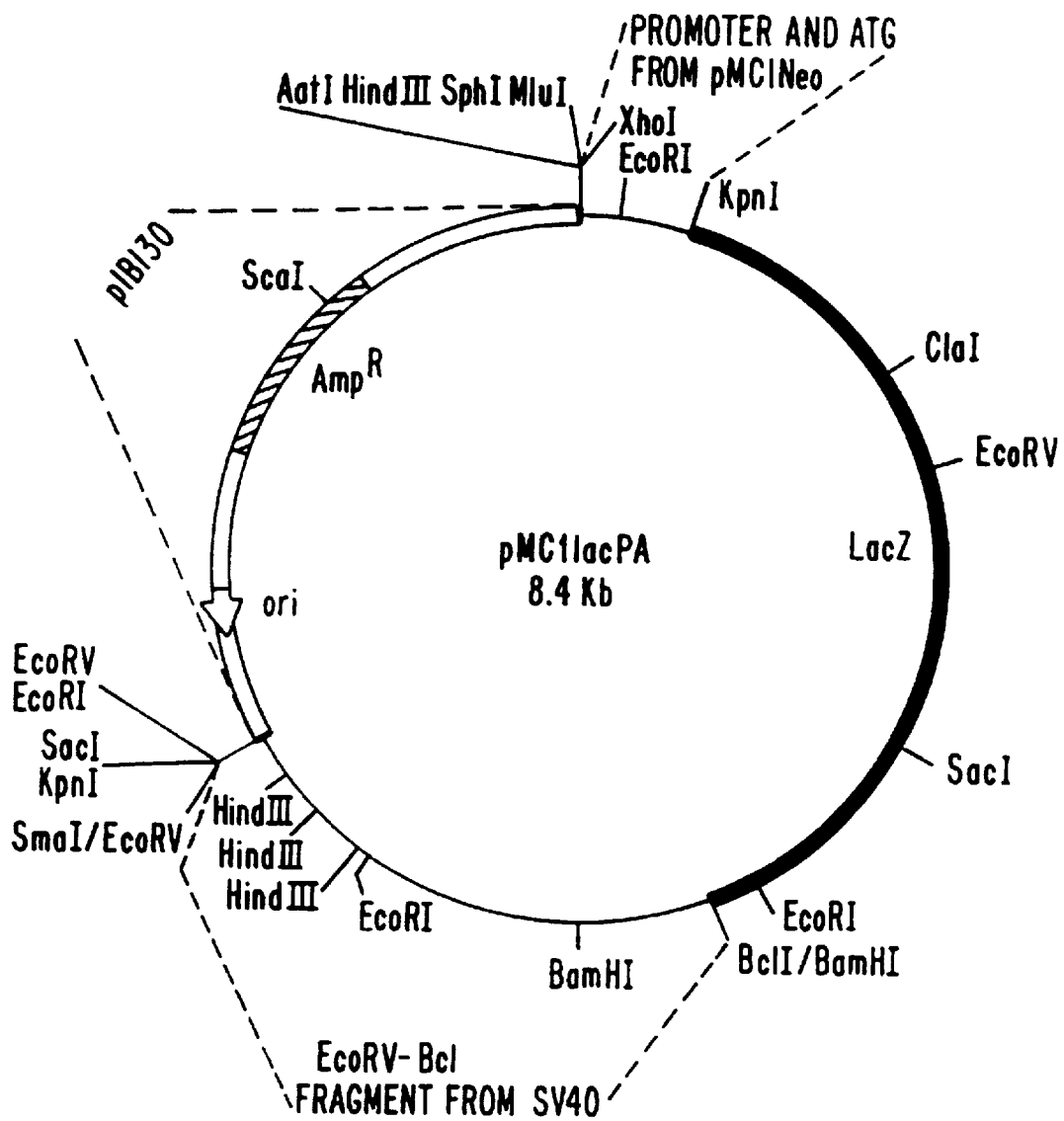
FIG._7

```
                                                    Eco RI
                            Eco RV    T7 RNA          V
                             V    POLYMERASE PROMOTER              pppGGGAGA...(RNA)-->
5'-ATG ATT ACG GAT ATC GAA TTA ATA CGA CTC ACT ATA GGG AGA TCG AAT TCG Sma I                 Hinc II
            Sac I   Xma I                  Acc I                     Xho I
             V      V V  Kpn I Bam HI Xba I  Sal I       Pst I    Xpa I  Mlu I
                          V    V      V      VVV          V       VV      V
AGC TCG GTA CCC GGG GAT CCT CTA GAG TCG ACC TGC AGG GGC CCT CGA GAC Hind III
            Sph I         T3 RNA                                Aat I
            V V         POLYMERASE PROMOTER                      V
GCG TGG CAT GCA AGC TTT CTC CCT TTA GTG AGG GTT AAT TAT AGG CCT AGC TTG-3'
              <--(RNA)...AGAGGGppp
```

FIG._8

```
                          bglI                              Hin fI
        3610      3620      3630      3640      3650      3660
        ATAAAAAACAACTGCTGACGCCGCTGCGCGATCAGTTCACCCGTGCACCGCTGGATAACG
                    ^ ^ ^ ^^ ^                    ^
                    Aha IIFnu4 HIDpnI          Apa LI
                    Hga I    Cfo I
                    HgiD I   Hha I
                        Fnu4 HIAcc II
                             HinP I
                              MboI
                             Sau3A I
        3670      3680      3690      3700      3710      3720
        ACATTGGCGTAAGTGAAGCGACCCGCATTGACCCTAACGCCTGGGTCGAACGCTGGAAGG
                                            ^     ^              ^
                                         Apy I  Taq I         Fnu4 HI
                                         BstNI
                                         Eco RII
                                         ScrF I
        3730      3740      3750      3760      3770      3780
        CGGCGGGCCATTACCAGGCCGAAGCAGCGTTGTTGCAGTGCACGGCAGATACACTTGCTG
        ^^^       ^    ^    ^                  ^
        DraII    Apy I     BbvI              Apa LI
         Asu I   BstNI    Fnu4 HI
         Cfr 131 Eco RII
         Sau96 I ScrF I
          Hae III  Hae III
          Pal I    Pal I
        3790      3800      3810      3820      3830      3840
        ATGCGGTGCTGATTACGACCGCTCACGCGTGGCAGCATCAGGGGAAAACCTTATTTATCA
         ^                   ^^       ^    ^
         Hin fI             Mlu I   BbvI
                           Acc IIFnu4 HI
                               SfaN I
        3850      3860      3870      3880      3890      3900
        GCCGGAAAACCTACCGGATTGATGGTAGTGGTCAAATGGCGATTACCGTTGATGTTGAAG
        ^         ^ ^                            ^
        Hpa II    Hpa II                       Hin fI
        Msp I     Msp I
                  Hin fI
        3910      3920      3930      3940      3950      3960
        TGGCGAGCGATACACCGCATCCGGCGCGGATTGGCCTGAACTGCCAGCTGGCGCAGGTAG
                  ^    ^ ^^ ^   ^            ^^  ^
                  SfaN I Cfo IHin fI       Pvu IICfo I
                     Hpa II    Hae III     Alu IHha I
                     Msp I     Pal I             HinP I
                       Hha I
                       HinP I
                       Acc II
        3970      3980      3990      4000      4010      4020
        CAGAGCGGGTAAACTGGCTCGGATTAGGGCCGCAAGAAAACTATCCCGACCGCCTTACTG
                          ^   ^^^                               ^
                          Hin fIHae III                       Fnu4 HI
                             Asu I
                             Cfr 131
                             Sau96 I
                             Pal I
```

FIG._9

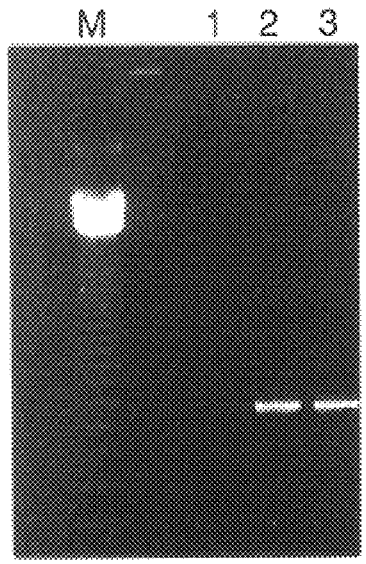
*FIG._10A*
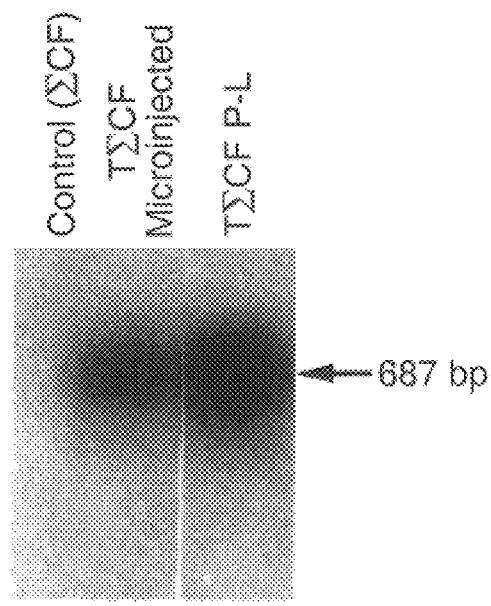
*FIG._10B*
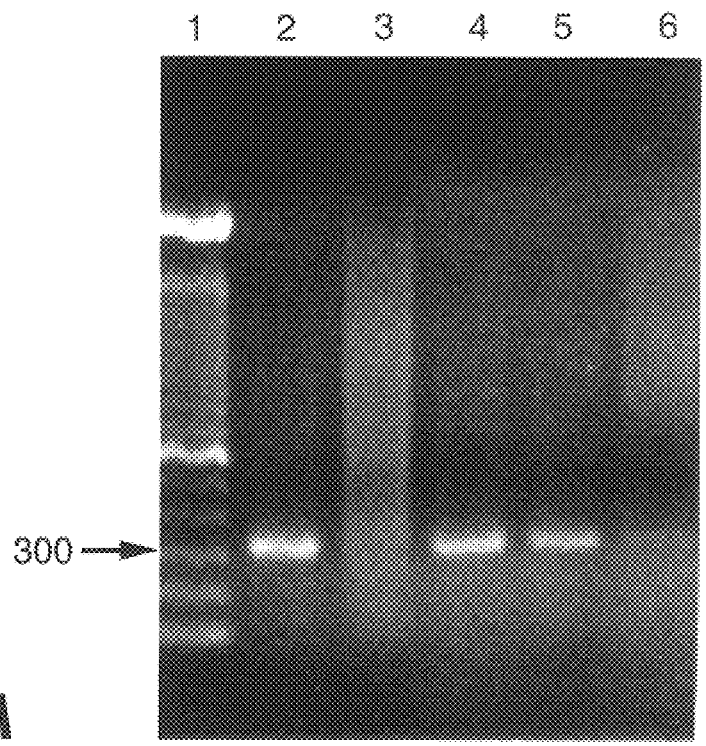
*FIG._11A*

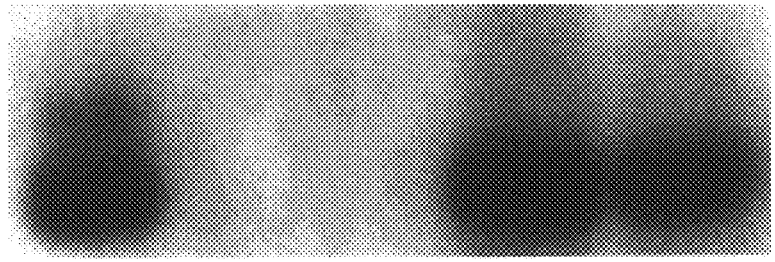
FIG._11B
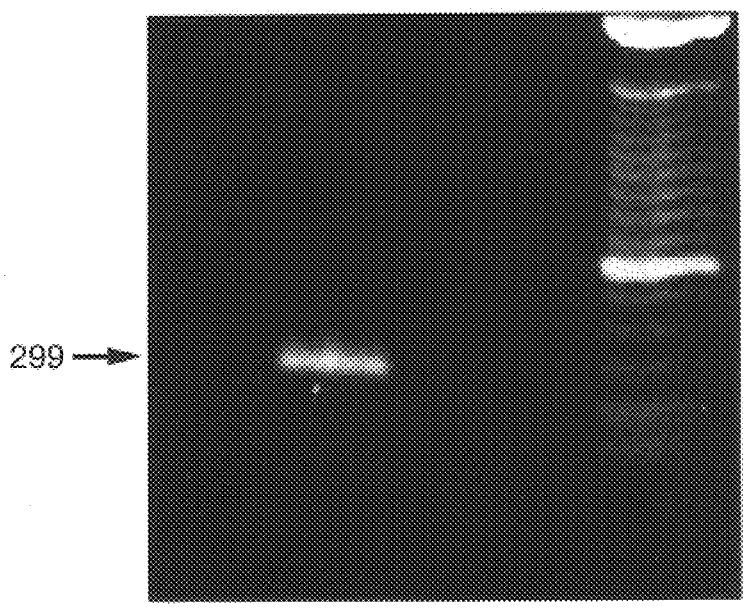
FIG._12

HOMOLOGOUS SEQUENCE TARGETING IN EUKARYOTIC CELLS

CROSS REFERENCE TO RELATED APPLICATION

This application is a continuation of Ser. No. 07/939,767 filed Sep. 2, 1992, now abandoned, which is a continuation-in-part of Ser. No. 07/873,438 filed Apr. 24, 1992 (now abandoned), all of which are incorporated herein by reference.

FIELD OF THE INVENTION

The invention relates to methods for targeting an exogenous polynucleotide or exogenous complementary polynucleotide pair to a predetermined endogenous DNA target sequence in a eukaryotic cell by homologous pairing, particularly for altering an endogenous DNA sequence, such as a chromosomal DNA sequence, typically by targeted homologous recombination. In certain embodiments, the invention relates to methods for targeting an exogenous polynucleotide having a linked chemical substituent to a predetermined endogenous DNA sequence in a metabolically active eukaryotic cell, generating a DNA sequence-specific targeting of one or more chemical substituents in an intact nucleus of a metabolically active eukaryotic cell, generally for purposes of altering a predetermined endogenous DNA sequence in the cell. The invention also relates to compositions that contain exogenous targeting polynucleotides, complementary pairs of exogenous targeting polynucleotides, chemical substituents of such polynucleotides, and recombinase proteins used in the methods of the invention.

BACKGROUND

Homologous recombination (or general recombination) is defined as the exchange of homologous segments anywhere along a length of two DNA molecules. An essential feature of general recombination is that the enzymes responsible for the recombination event can presumably use any pair of homologous sequences as substrates, although some types of sequence may be favored over others. Both genetic and cytological studies have indicated that such a crossing-over process occurs between pairs of homologous chromosomes during meiosis in higher organisms.

Alternatively, in site-specific recombination, exchange occurs at a specific site, as in the integration of phage $\lambda$ into the *E. coli* chromosome and the excision of $\lambda$ DNA from it. Site-specific recombination involves specific sequences of the phage DNA and bacterial DNA. Within these sequences there is only a short stretch of homology necessary for the recombination event, but not sufficient for it. The enzymes involved in this event generally cannot recombine other pairs of homologous (or nonhomologous) sequences, but act specifically on the particular phage and bacterial sequences.

Although both site-specific recombination and homologous recombination are useful mechanisms for genetic engineering of DNA sequences, targeted homologous recombination provides a basis for targeting and altering essentially any desired sequence in a duplex DNA molecule, such as targeting a DNA sequence in a chromosome for replacement by another sequence. Site-specific recombination has been proposed as one method to integrate transfected DNA at chromosomal locations having specific recognition sites (O'Gorman et al. (1991) *Science* 251: 1351; Onouchi et al. (1991) *Nucleic Acids Res.* 19: 6373). Unfortunately, since this approach requires the presence of specific target sequences and recombinases, its utility for targeting recombination events at any particular chromosomal location is severely limited in comparison to targeted general recombination.

For these reasons and others, targeted homologous recombination has been proposed for treating human genetic diseases. Human genetic diseases include: (1) classical human genetic diseases wherein a disease allele having a mutant genetic lesion is inherited from a parent (e.g., adenosine deaminase deficiency, sickle cell anemia, thalassemias), (2) complex genetic diseases like cancer, where the pathological state generally results from one or more specific inherited or acquired mutations, and (3) acquired genetic disease, such as an integrated provirus (e.g., hepatitis B virus). However, current methods of targeted homologous recombination are inefficient and produce desired homologous recombinants only rarely, necessitating complex cell selection schemes to identify and isolate correctly targeted recombinants.

A primary step in homologous recombination is DNA strand exchange, which involves a pairing of a DNA duplex with at least one DNA strand containing a complementary sequence to form an intermediate recombination structure containing heteroduplex DNA (see, Radding, C. M. (1982) *Ann. Rev. Genet.* 16: 405; U.S. Pat. No. 4,888,274). The heteroduplex DNA may take several forms, including a triplex form wherein a single complementary strand invades the DNA duplex (Hsieh et al. (1990) *Genes and Development* 4: 1951) and, when two complementary DNA strands pair with a DNA duplex, a classical Holliday recombination joint or chi structure (Holliday, R. (1964) *Genet. Res.* 5: 282) may form, or a double-D loop ("Diagnostic Applications of Double-D Loop Formation" U.S. Ser. No. 07/755,462, filed Sep. 4, 1991, which is incorporated herein by reference). Once formed, a heteroduplex structure may be resolved by strand breakage and exchange, so that all or a portion of an invading DNA strand is spliced into a recipient DNA duplex, adding or replacing a segment of the recipient DNA duplex. Alternatively, a heteroduplex structure may result in gene conversion, wherein a sequence of an invading strand is transferred to a recipient DNA duplex by repair of mismatched bases using the invading strand as a template (*Genes*, 3rd Ed. (1987) Lewin, B., John Wiley, New York, N.Y.; Lopez et al. (1987) *Nucleic Acids Res.* 15: 5643). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules makes targeted homologous recombination a powerful method in genetic engineering and gene manipulation.

The ability of mammalian and human cells to incorporate exogenous genetic material into genes residing on chromosomes has demonstrated that these cells have the general enzymatic machinery for carrying out homologous recombination required between resident and introduced sequences. These targeted recombination events can be used to correct mutations at known sites, replace genes or gene segments with defective ones, or introduce foreign genes into cells. The efficiency of such gene targeting techniques is related to several parameters: the efficiency of DNA delivery into cells, the type of DNA packaging (if any) and the size and conformation of the incoming DNA, the length and position of regions homologous to the target site (all these parameters also likely affect the ability of the incoming homologous DNA sequences to survive intracellular nuclease attack), the efficiency of recombination at particular chromosomal sites and whether recombinant events are homologous or nonhomologous. Over the past 10 years or so, several methods have been developed to introduce DNA into mammalian cells: direct needle microinjection, transfection, electroporation, retroviruses, adenoviruses, and other viral packaging and delivery systems, liposomes, and most recently techniques using DNA-coated microprojectiles delivered with a gene gun (called a biolistics device), or narrow-beam lasers (laser-poration). The processes associated with some types of gene transfer have been shown to be both mutagenic and carcinogenic (Bardwell, (1989) *Mutagenesis* 4:245), and these possibilities must be considered in choosing a transfection approach.

The choice of a particular DNA transfection procedure depends upon its availability to the researcher, the technique's efficiency with the particular chosen target cell type, and the researchers concerns about the potential for generating unwanted genome mutations. For example, retroviral integration requires dividing cells, most often results in nonhomologous recombination events, and retroviral insertion within a coding sequence of nonhomologous (i.e., non-targeted) gene could cause cell mutation by inactivating the gene's coding sequence (Friedmann, (1989) *Science* 244:1275). Newer retroviral-based DNA delivery systems are being developed using defective retroviruses. However, these disabled viruses must be packaged using helper systems, are often obtained at low titer, and recombination is still not site-specific, thus recombination between endogenous cellular retrovirus sequences and disabled virus sequences could still produce wild-type retrovirus capable of causing gene mutation. Adeno- or polyoma virus based delivery systems appear very promising (Samulski et al., (1991) *EMBO J.* 10: 3941; Gareis et al., (1991) *Cell. Molec. Bio.* 37: 191; Roesnfeld et al. (1992) *Cell* 68: 143) although they still require specific cell membrane recognition and binding charactiersistics for target cell entry. Liposomes often show a narrow spectrum of cell specificities, and when DNA is coated externally on to them, the DNA is often sensitive to cellular nucleases. Newer polycationic liposper- mines compunds exhibit broad cell ranges (Behr et al., (1989) *Proc. Natl. Acad. Sci. USA* 86:6982) and DNA is coated by these compounds. In addition, a combination of neutral and cationic lipid has been shown to be highly efficient at transfection of animal cells and showed a broad spectrum of effectiveness in a variety of cell lines (Rose et al., (1991) *BioTechniques* 10:520). Galactosylated bis-acridine has also been described as a carrier for delivery of polynucleotides to liver cells (Haensler JL and Szoka FC (1992), Abstract V211 in *J. Cell. Biochem.* Supplement 16F, Apr. 3–16, 1992, incorporated herein by reference). Electroporation also appears to be applicable to most cell types. The efficiency of this procedure for a specific gene is variable and can range from about one event per $3\times10^4$ transfected cells (Thomas and Capecchi, (1987) *Cell* 51:503) to between one in $10^7$ and $10^8$ cells receiving the exogenous DNA (Koller and Smithies, (1989) *Proc. Natl. Acad. Sci. (U.S.A.)* 86: 8932). Microinjection of exogenous DNA into the nucleus has been reported to result in a high frequency of stable transfected cells. Zimmer and Gruss (Zimmer and Gruss (1989) *Nature* 338: 150) have reported that for the mouse hox1.1 gene, 1 per 150 microinjected cells showed a stable homologous site specific alteration.

Several methods have been developed to detect and/or select for targeted site-specific recombinants between vector DNA and the target homologous chromosomal sequence (see, Capecchi, (1989) *Science* 244:1288 for review). Cells which exhibit a specific phenotype after site-specific recombination, such as occurs with alteration of the hprt gene, can be obtained by direct selection on the appropriate growth medium. Alternatively, a selective marker sequence such as neo can be incorporated into a vector under promoter control, and successful transfection can be scored by selecting $G418^r$ cells followed by PCR to determine whether neo is at the targeted site (Joyner et al., (1989) *Nature* 338:153). A positive-negative selection (PNS) procedure using both neo and HSV-tk genes allows selection for transfectants and against non-homologous recombination events, and significantly enriched for desired disruption events at several different mouse genes (Mansour et al., (1988) *Nature* 336:348). This procedure has the advantage that the method does not require that the targeted gene be transcribed. If the targeted gene is transcribed, a promoter-less marker gene can be incorporated into the targeting construct so that the gene becomes activated after homologous recombination with the target site (Jasin and Berg, (1988) *Genes and Development* 2:1353; Doetschman et al. (1988) *Proc. Natl. Acad. Sci, (U.S.A.)* 85: 8583; Dorini et al., (1989) *Science* 243:1357; Itzhaki and Porter, (1991) *Nucl. Acids Res.* 19:3835). Recombinant products produced using vectors with selectable markers often continue to retain these markers as foreign genetic material at the site of transfection, although loss does occur. Valancius and Smithies (Valancius and Smithies, (1991) *Molec. Cellular Biol.* 11:1402) have recently described an "in-out" targeting procedure that allowed a subtle 4-bp insertion modification of a mouse hprt target gene. The resulting transfectant contained only the desired modified gene sequence and no selectable marker remained after the "out" recombination step. Cotransformation of cells with two different vectors, one vector contained a selectable gene and the other used for gene disruption, increases the efficiency of isolating a specific targeting reaction (Reid et al., (1991) *Molec. Cellular Biol.* 11:2769) among selected cells that are subsequently scored for stable recombinants.

Unfortunately, exogenous sequences transferred into eukaryotic cells undergo homologous recombination with homologous endogenous sequences only at very low frequencies, and are so inefficiently recombined that large numbers of cells must be transfected, selected, and screened in order to generate a desired correctly targeted homologous recombinant (Kucherlapati et al. (1984) *Proc. Natl. Acad. Sci. (U.S.A.)* 81: 3153; Smithies, O (1985) *Nature* 317: 230; Song et al. (1987) *Proc. Natl. Acad. Sci. (U.S.A.)* 84: 6820; Doetschman et al. (1987) *Nature* 330: 576; Kim and Smithies (1988) *Nucleic Acids Res.* 16: 8887; Doetschman et al. (1988) op.cit.; Koller and Smithies (1989) op.cit.; Shesely et al. (1991) *Proc. Natl. Acad. Sci. (U.S.A.)* 88: 4294; Kim et al. (1991) *Gene* 103: 227, which are incorporated herein by reference).

Recently, Koller et al. (1991) *Proc. Natl. Acad. Sci. (U.S.A.)* 88: 10730 and Snouwaert et al. (1992) *Science* 257: 1083, have described targeting of the mouse cystic fibrosis transmembrane regulator (CFTR) gene for the purpose of inactivating, rather than correcting, a murine CFTR allele. Koller et al. employed a large (7.8 kb) homology region in the targeting construct, but nonetheless reported a low frequency for correct targeting (only 1 of 2500 G418-resistant cells were correctly targeted). Thus, even targeting constructs having long homology regions are inefficiently targeted.

Several proteins or purified extracts having the property of promoting homologous recombination (i.e., recombinase activity) have been identified in prokaryotes and eukaryotes (Cox and Lehman (1987) *Ann. Rev. Biochem.* 56:229; Radding, C. M. (1982) op.cit.; Madiraju et al. (1988) *Proc. Natl. Acad. Sci. (U.S.A.)* 85: 6592; McCarthy et al. (1988) *Proc. Natl. Acad. Sci. (U.S.A.)* 85: 5854; Lopez et al. (1987) op.cit., which are incorporated herein by reference). These general recombinases presumably promote one or more steps in the formation of homologously-paired intermediates, strand-exchange, gene conversion, and/or other steps in the process of homologous recombination.

The frequency of homologous recombination in prokaryotes is significantly enhanced by the presence of recombinase activities. Several purified proteins catalzye homologous pairing and/or strand exchange in vitro, including: *E. coli* recA protein, the T4 uvsX protein, and the rec1 protein from *Ustilago maydis*. Recombinases, like the recA protein of *E. coli* are proteins which promote strand pairing and exchange. The most studied recombinase to date has been the recA recombinase of *E. coli*, which is involved in homology search and strand exchange reactions (see, Cox and Lehman (1987) op.cit.). RecA is required for induction of the SOS repair response, DNA repair, and efficient genetic recombination in *E. coli*. RecA can catalyze homologous pairing of a linear duplex DNA and a homologous single strand DNA in vitro. In contrast to site-specific recombinases, proteins like recA which are involved in general recombination recognize and promote pairing of DNA structures on the basis of shared homology, as has been shown by several in vitro experiments (Hsieh and Camerini-Otero (1989) *J. Biol. Chem.* 264: 5089; Howard-Flanders et al. (1984) *Nature* 309: 215; Stasiak et al. (1984) *Cold Spring Harbor Symp. Quant. Biol.* 49: 561; Register et al. (1987) *J. Biol. Chem.* 262: 12812). Several investigators have used recA protein in vitro to promote homologously paired triplex DNA (Cheng et al. (1988) *J. Biol. Chem.* 263: 15110; Ferrin and Camerini-Otero (1991) *Science* 354: 1494; Ramdas et al. (1989) *J. Biol. Chem.* 264: 17395; Strobel et al. (1991) *Science* 254: 1639; Hsieh et al. (1990) op.cit.; Rigas et al. (1986) *Proc. Natl. Acad. Sci. (U.S.A.)* 83: 9591; and Camerini-Otero et al. U.S. Pat. No. 7,611,268 (available from Derwent), which are incorporated herein by reference). Unfortunately, many important genetic engineering manipulations involving homologous recombination, such as using homologous recombination to alter endogenous DNA sequences in a living cell, cannot be done in vitro. Further, gene therapy requires highly efficient homologous recombination of targeting vectors with predetermined endogenous target sequences, since selectable marker selection schemes such as those currently available in the art are not usually practicable in human beings.

Thus, there exists a need in the art for methods of efficiently altering predetermined endogenous genetic sequences by homologous pairing and homologous recombination in vivo by introducing one or more exogenous targeting polynucleotide(s) that efficiently and specifically homologously pair with a predetermined endogenous DNA sequence. There exists a need in the art for high-efficiency gene targeting, so that complex in vitro selection protocols (e.g., neo gene selection with G418) which are of limited utility for in vivo gene therapy on affected individuals, are avoided.

SUMMARY OF THE INVENTION

It is an object of the present invention to provide methods for targeting an exogenous polynucleotide to a predetermined endogenous DNA target sequence in a eukaryotic cell with high efficiency and with sequence specificity. Exogenous polynucleotides, are localized (or targeted) to one or more predetermined DNA target sequence(s) by homologous pairing in vivo. Such targeted homologous pairing of exogenous polynucleotides to endogenous DNA sequences in vivo may be used: (1) to target chemical substituents in a sequence-specific specific manner in vivo, (2) to correct or to generate genetic mutations in endogenous DNA sequences by homologous recombination and/or gene conversion, (3) to produce homologously targeted transgenic animals at high efficiency, and (4) in other applications (e.g., targeted drug delivery) based on in vivo homologous pairing. Some embodiments of the invention employ targeted exogenous polynucleotides to correct endogenous mutant gene alleles in human cells; the invention provides methods and compositions for correcting disease alleles involved in producing human genetic diseases, such as inherited genetic diseases (e.g., cystic fibrosis) and neoplasia (e.g., neoplasms induced by somatic mutation of an oncogene or tumor suppressor gene, such as p53, or viral genes associated with neoplasia, such as HBV genes).

In one embodiment, at least one exogenous polynucleotide is targeted to a predetermined endogenous DNA sequence and alters the endogenous DNA sequence, such as a chromosomal DNA sequence, typically by targeted homologous recombination within and/or flanking the predetermined endogenous DNA sequence. Generally, two complementary exogenous polynucleotides are used for targeting an endogenous DNA sequence. Typically, the targeting polynucleotide(s) are introduced simultaneously or contemporaneously with one or more recombinase species. Alternatively, one or more recombinase species may be produced in vivo by expression of a heterologous expression cassette in a cell containing the preselected target DNA sequence.

It is another object of the invention to provide methods whereby at least one exogenous polynucleotide containing a chemical substituent can be targeted to a predetermined endogenous DNA sequence in a metabolically-active eukaryotic cell, permitting sequence-specific targeting of chemical substituents such as, for example: cross-linking agents, metal chelates (e.g., iron/EDTA chelate for iron catalyzed cleavage), topoisomerases, endonucleases, exonucleases, ligases, phosphodiesterases, photodynamic porphyrins, free-radical generating drugs, chemotherapeutic drugs (e.g., adriamycin, doxirubicin), intercalating agents, base-modification agents, immunoglobulin chains, oligonucleotides, and other substituents. The methods of the invention can be used to target such a chemical substituent to a predetermined DNA sequence by homologous pairing for various applications, for example: producing sequence-specific strand scission(s), producing sequence-specific chemical modifications (e.g., base methylation, strand cross-linking), producing sequence-specific localization of polypeptides (e.g., topoisomerases, helicases, proteases), producing sequence-specific localization of polynucleotides (e.g., loading sites for transcription factors and/or RNA polymerase), and other applications.

It is another object of the present invention to provide methods for correcting a genetic mutation in an endogenous DNA target sequence, such as a sequence encoding a protein. For example, the invention can be used to correct genetic mutations, such as base substitutions, additions, and/or deletions, by converting a mutant DNA sequence that encodes a non-functional, dysfunctional, and/or truncated polypeptide into a corrected DNA sequence that encodes a functional polypeptide (e.g., has a biological activity such as an enzymatic activity, hormone function, or other biological property). The methods and compositions of the invention may also be used to correct genetic mutations or dysfunctional alleles with genetic lesions in non-coding sequences (e.g., promoters, enhancers, silencers, origins of replication, splicing signals). In contradistinction, the invention also can be used to target DNA sequences for inactivating gene expression; a targeting polynucleotide can be employed to make a targeted base substitution, addition, and/or deletion in a structural or regulatory endogenous DNA sequence to alter expression of one or more genes, typically by knocking out at least one allele of a gene (i.e., making a mutant, nonfunctional allele). The invention can also be used to correct disease alleles, such as a human or non-human animal CFTR gene allele associated with cystic fibrosis, by producing a targeted alteration in the disease allele to correct a disease-causing lesion (e.g., a deletion).

It is a further object of the invention to provide methods and compositions for high-efficiency gene targeting of human genetic disease alleles, such as a CFTR allele associated with cystic fibrosis or an LDL receptor allele associated with familial hypercholesterolemia. In one aspect of the invention, targeting polynucleotides having at least one associated recombinase are targeted to cells in vivo (i.e., in an intact animal) by exploiting the advantages of a receptor-mediated uptake mechanism, such as an asialoglycoprotein receptor-mediated uptake process. In this variation, a targeting polynucleotide is associated with a recombinase and a cell-uptake component which enhances the uptake of the targeting polynucleotide-recombinase into cells of at least one cell type in an intact individual. For example, but not limitation, a cell-uptake component typically consists essentially of: (1) a galactose-terminal (asialo-) glycoprotein (e.g., asialoorosomucoid) capable of being recognized and internalized by specialized receptors (asialoglycoprotein receptors) on hepatocytes in vivo, and (2) a polycation, such as poly-L-lysine, which binds to the targeting polynucleotide, usually by electrostatic interaction. Typically, the targeting polynucleotide is coated with recombinase and cell-uptake component simultaneously so that both recombinase and cell-uptake component bind to the targeting polynucleotide; alternatively, a targeting polynucleotide can be coated with recombinase prior to incubation with a cell-uptake component; alternatively the targeting polynucleotide can be coated with the cell-uptake component and introduced into cells comtemporaneously with a separately delivered recombinase (e.g., by targeted liposomes containing one or more recombinase).

The invention also provides methods and compositions for treatment and prophylaxis of genetic diseases of animals, particularly mammals, wherein a recombinase and a targeting polynucleotide are used to produce a targeted sequence modification in a disease allele of an endogenous gene. The invention may also be used to produce targeted sequence modification(s) in a non-human animal, particularly a non-human mammal such as a mouse, which create(s) a disease allele in a non-human animal. Sequence-modified non-human animals harboring such a disease allele may provide useful models of human and veterinary disease(s). Alternatively, the methods and compositions of the invention can be used to provide non-human animals having homologously-targeted human disease alleles integrated into a non-human genome; such non-human animals may provide useful experimental models of human genetic disease, including neoplastic diseases.

It is also an object of the invention to provide methods and compositions for recombinase-enhanced positioning of a targeting polynucleotide to a homologous sequence in an endogenous chromosome to form a stable multistrand complex, and thereby alter expression of a predetermined gene sequence by interfering with transcription of sequence(s) adjacent to the multistrand complex. Recombinase(s) are used to ensure correct homologous pairing and formation of a stable multistrand complex, which may include a double-D loop structure. For example, a targeting polynucleotide coated with a recombinase may homologously pair with an endogenous chromosomal sequence in a structural or regulatory sequence of a gene and form a stable multistrand complex which may: (1) constitute a significant physical or chemical obstacle to formation of or procession of an active transcriptional complex comprising at least an RNA polymerase, or (2) alter the local chromatin structure so as to alter the transcription rate of gene sequences within about 1 to 500 kilobases of the multistrand complex.

It is another object of the invention to provide methods and compositions for treating or preventing human and animal diseases, particularly viral diseases, such as human hepatitis B virus (HBV) hepatitis, by targeting viral gene sequences with a recombinase-associated targeting polynucleotide and thereby inactivating said viral gene sequences and inhibiting viral-induced pathology.

It is a further object of the invention to provide compositions that contain exogenous targeting polynucleotides, complementary pairs of targeting polynucleotides, chemical substituents of such polynucleotides, and recombinase proteins used in the methods of the invention. Such compositions may include cell-uptake components to facilitate intracellular uptake of a targeting polynucleotide, especially for in vivo gene therapy and gene modification.

BRIEF DESCRIPTION OF THE DRAWINGS

FIG. 1. Homologous targeting of recA-coated chromosome 1 alpha-satellite polynucleotides in living cell nuclei. The homologously targeted biotinylated polynucleotides were visualized by addition of FITC-avidin followed by washing to remove unbound FITC. Signals were visualized using a Zeiss Confocal Laser Scanning Microscope (CLSM) with 488 nm argon laser beam illumination for FITC-DNA detection. Top left—localized FITC-DNA signals in cell nucleus. Lower left—enhanced image of FITC-DNA signals in cell nucleus. Upper right—image of FITC-DNA signals overlaid on phase image of nucleus. Lower right—phase image of center of cell nucleus showing nucleoli. Note: all images except lower right were photographed at same focus level (focus unchanged between these photos).

FIG. 2. Homologous targeting of recA-coated chromosome 1 alpha-satellite polynucleotides in living cell nuclei. Bottom—fluorescent image of FITC-DNA signals in cell nucleus. Middle—enhanced image of FITC-DNA signal in cell nucleus. Top—overlay of FITC-DNA signals on phase image of nucleus.

FIG. 3. Decondensed DNA from a targeted human chromosome 1 in a living cell nucleus displaying repeated alpha-satellite DNA sequences as visualized by FITC labeling.

FIG. 4. FITC—localization of recA-coated polynucleotides targeted to human chromosome 1 alpha-satellite sequences in a living cell nucleus. Top—image of enhanced FITC-signals. Bottom—overlay of FITC-signals on phase contrast image of cell nucleus.

FIG. 5. Human p53 tumor suppressor gene targeting in living HEp-2 cell nuclei.

FIG. 6. Map of mammalian expression lacZ plasmid pMC1lacXpA.

FIG. 7. Map of mammalian expression lacZ plasmid pMC1lacpA.

FIG. 8. Multiple cloning site of plasmid pIBI30.

FIG. 9. PCR products and primers from lacZ gene sequence.

FIG. 10A. Southern hybridization analysis of the 687-bp fragment amplified from genomic DNA. Electrophoretic migration of a 687-bp DNA fragment generated with primers CF1 and CF6 from genomic DNA of ΣCFTE29o-cells which were capillary needle-microinjected with the 491-nucleotide fragment in the presence of recA (lane 2) or transfected as a protein-DNA-lipid complex where the 491-nucleotide fragments were coated with recA (+; lane 3). The control DNA was amplified from nontransfected ΣCFTE29o-cultures (lane 1).

FIG. 10B Autoradiographic analysis of DNA transferred to Gene Screen Plus filters and hybridized with a $^{32}$P-labeled oligonucleotide specific for normal exon 10 sequences in the region of the ΔF508 mutation. Cells transfected by microinjection or protein-lipid-DNA complexes both were positive for homologous targeting, whereas control cells were not.

FIG. 11A. Analysis of DNA from cells electroporated or transfected with DNA encapsulated in a protein-lipid complex. Allele-specific PCR amplification of the 687/684 bp DNA fragment amplified in the first round with primers CF1 and oligo N (N) or oligo ΔF (ΔF). Ethidium bromide-stained 300 bp DNA fragment separated by electrophoresis in a 1% agarose gel. The DNA in each lane is as follows: lane 1, 100-bp marker DNA; lane 2, control 16HBE14o-cell DNA amplified with the CF1/N primer pair; lane 3, nontransfected ΣCFTE29o-cell DNA amplified with CF1/N primers; lane 4, nontransfected ΣCFTE29o-cell DNA amplified with CF1/ΔF primers; lane 5, DNA from ΣCFTE29o-cells electroporated with recA-coated 491-nucleotide fragments and amplified with CF1/N primers; lane 6, DNA from ΣCFTE29o-cells transfected with recA-coated 491-nucleotide fragment encapsulated in a protein-lipid complex and amplified with CF1/N.

FIG. 11B Autoradiographic analysis of the DNA in FIG. 11A transferred to Gene Screen Plus filters and hybridized with $^{32}$P-labeled oligo N probe. Samples in lanes 1–5 for the autoradiographic analysis are equivalent to lanes 2–6 in FIG. 11A.

FIG. 12. PCR analysis of ΣCFTE29o-genomic DNA reconstructed with the addition of 2×10$^5$ copies of recA-coated 491-nucleotide fragments per microgram of genomic DNA. This number of DNA fragments represents the total number of DNA copies microinjected into cells and tests whether the 491-nucleotide fragment can act as a primer for the 687/684-bp fragment amplification. DNA was amplified as described in FIG. 10A. When the second round of amplification was conducted with CF1 and the oligo N primers (lane 2), the 300-bp DNA band was not detected when aliquots of the amplification reaction were separated electrophoretically. Amplification of the ΣCFTE29o-/491 bp DNA fragment with the CF1/oligo ΔF primer pair produced a 299-bp DNA product (lane 1). Marker DNA is in lane 3.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis,* 2nd Edition, E. S. Golub and D. R. Green, Eds., Sinauer Associates, Sunderland, Mass. (1991), which is incorporated herein by reference).

As used herein, the terms "predetermined endogenous DNA sequence" and "predetermined target sequence" refer to polynucleotide sequences contained in a eukaryotic cell. Such sequences include, for example, chromosomal sequences (e.g., structural genes, promoters, enhancers, recombinatorial hotspots, repeat sequences, integrated proviral sequences), episomal sequences (e.g., replicable plasmids or viral replication intermediates), chloroplast and mitochondrial DNA sequences. By "predetermined" it is meant that the target sequence may be selected at the discretion of the practitioner on the basis of known or predicted sequence information, and is not constrained to specific sites recognized by certain site-specific recombinases (e.g., FLP recombinase or CRE recombinase). In some embodiments, the predetermined endogenous DNA target sequence will be other than a naturally occurring germline DNA sequence (e.g., a transgene, parasitic, or mycoplasmal or viral sequence). An exogenous polynucleotide is a polynucleotide which is transferred into a eukaryotic cell but which has not been replicated in that host cell; for example, a virus genome polynucleotide that enters a cell by fusion of a virion to the cell is an exogenous polynucleotide, however, replicated copies of the viral polynucleotide subsequently made in the infected cell are endogenous sequences (and may, for example, become integrated into a cell chromosome). Similarly, transgenes which are microinjected or transfected into a cell are exogenous polynucleotides, however integrated and replicated copies of the transgene(s) are endogenous sequences.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The terms "substantially corresponds to" or "substantial identity" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. "Substantially complementary" as used herein refers to a sequence that is complementary to a sequence that substantially corresponds to a reference sequence. In general, targeting efficiency increases with the length of the targeting polynucleotide portion that is substantially complementary to a reference sequence present in the target DNA.

"Specific hybridization" is defined herein as the formation of hybrids between a targeting polynucleotide (e.g., a polynucleotide of the invention which may include substitutions, deletion, and/or additions as compared to the predetermined target DNA sequence) and a predetermined target DNA, wherein the targeting polynucleotide preferentially hybridizes to the predetermined target DNA such that, for example, at least one discrete band can be identified on a Southern blot of DNA prepared from eukaryotic cells that contain the target DNA sequence, and/or a targeting polynucleotide in an intact nucleus localizes to a discrete chromosomal location characteristic of a unique or repetitive sequence. In some instances, a target sequence may be present in more than one target polynucleotide species (e.g., a particular target sequence may occur in multiple members of a gene family or in a known repetitive sequence). It is evident that optimal hybridization conditions will vary depending upon the sequence composition and length(s) of the targeting polynucleotide(s) and target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif., which are incorporated herein by reference. Methods for hybridizing a targeting polynucleotide to a discrete chromosomal location in intact nuclei are provided herein in the Detailed Description.

The term "naturally-occurring" as used herein as applied to an object refers to the fact that an object can be found in nature. For example, a polynucleotide sequence that is present in an organism (including viruses) that can be isolated from a source in nature and which has not been intentionally modified by man in the laboratory is naturally-occurring.

A metabolically-active cell is a cell, comprising an intact nucleus, which, when provided nutrients and incubated in an appropriate medium carries out DNA synthesis and RNA for extended periods (e.g., at least 12–24 hours). Such metabolically-active cells are typically differentiated cells incapable of further cell division (although nuclear division and chromosomal replication may occur), although stem cells are also metabolically-active cells.

As used herein, the term "disease allele" refers to an allele of a gene which is capable of producing a recognizable disease. A disease allele may be dominant or recessive and may produce disease directly or when present in combination with a specific genetic background or pre-existing pathological condition. A disease allele may be present in the gene pool or may be generated de novo in an individual by somatic mutation. For example and not limitation, disease alleles include: activated oncogenes, a sickle cell anemia allele, a Tay-Sachs allele, a cystic fibrosis allele, a Lesch-Nyhan allele, a retinoblastoma-susceptibility allele, a Fabry's disease allele, and a Huntington's chorea allele. As used herein, a disease allele encompasses both alleles associated with human diseases and alleles associated with recognized veterinary diseases. For example, the ΔF508 CFTR allele is a human disease allele which is associted with cystic fibrosis.

As used herein, the term "cell-uptake component" refers to an agent which, when bound, either directly or indirectly, to a targeting polynucleotide, enhances the intracellular uptake of the targeting polynucleotide into at least one cell type (e.g., hepatocytes). A cell-uptake component may include, but is not limited to, the following: a galactose-terminal (asialo-) glycoprotein capable of being internalized into hepatocytes via a hepatocyte asialoglycoprotein receptor, a polycation (e.g., poly-L-lysine), and/or a protein-lipid complex formed with the targeting polynucleotide. Various combinations of the above, as well as alternative cell-uptake components will be apparent to those of skill in the art and are provided in the published literature.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgenesis. Generally enzymatic reactions, oligonucleotide synthesis, oligonucleotide modification, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Transgenic mice are derived according to Hogan, et al., "Manipulating the Mouse Embryo: A Laboratory Manual", Cold Spring Harbor Laboratory (1988) which is incorporated herein by reference.

Embryonic stem cells are manipulated according to published procedures (Teratocarcinomas and embryonic stem cells: a practical approach, E. J. Robertson, ed., IRL Press, Washington, D.C., 1987; Zjilstra et al., *Nature* 342:435–438 (1989); and Schwartzberg et al., *Science* 246:799–803 (1989), each of which is incorporated herein by reference).

Oligonucleotides can be synthesized on an Applied Bio Systems oligonucleotide synthesizer according to specifications provided by the manufacturer.

Targeting Polynucleotides

Targeting polynucleotides may be produced by chemical synthesis of oligonucleotides, nick-translation of a double-stranded DNA template, polymerase chain-reaction amplification of a sequence (or ligase chain reaction amplification), purification of prokaryotic or eukaryotic cloning vectors harboring a sequence of interest (e.g., a cloned cDNA or genomic clone, or portion thereof) such as plasmids, phagemids, YACs, cosmids, bacteriophage DNA, other viral DNA or replication intermediates, or purified restriction fragments thereof, as well as other sources of single and double-stranded polynucleotides having a desired nucleotide sequence. Targeting polynucleotides are generally ssDNA or dsDNA, most preferably dsDNA.

Targeting polynucleotides are generally at least about 50 to 100 nucleotides long, preferably at least about 250 to 500 nucleotides long, more preferably at least about 1000 to 2000 nucleotides long, or longer; however, as the length of a targeting polynucleotide increases beyond about 20,000 to 50,000 nucleotides, the efficiency of transferring an intact targeting polynucleotide into the cell decreases. The length of homology may be selected at the discretion of the practitioner on the basis of the sequence composition and complexity of the predetermined endogenous target DNA sequence(s) and guidance provided in the art, which generally indicates that 1.3 to 6.8 kilobase segments of homology are preferred (Hasty et al. (1991) *Molec. Cell. Biol.* 11: 5586; Shulman et al. (1990) *Molec. Cell. Biol.* 10: 4466, which are incorporated herein by reference). Targeting polynucleotides have at least one sequence that substantially corresponds to, or is substantially complementary to, a predetermined endogenous DNA sequence (i.e., a DNA sequence of a polynucleotide located in a eukaryotic cell, such as a chromosomal, mitochondrial, chloroplast, viral, episomal, or mycoplasmal polynucleotide). Such targeting polynucleotide sequences serve as templates for homologous pairing with the predetermined endogenous sequence(s), and are also referred to herein as homology clamps. In targeting polynucleotides, such homology clamps are typically located at or near the 5' or 3' end, preferably homology clamps are located at each end of the polynucleotide (Berinstein et al. (1992) *Molec. Cell. Biol.* 12: 360, which is incorporated herein by reference). Without wishing to be bound by any particular theory, it is believed that the addition of recombinases permits efficient gene targeting with targeting polynucleotides having short (i.e., about 50 to 500 basepair long) segments of homology, as well as with targeting polynucleotides having longer segments of homology.

The formation of heteroduplex joints is not a stringent process; genetic evidence supports the view that the classical phenomena of meiotic gene conversion and aberrant meiotic segregation result in part from the inclusion of mismatched base pairs in heteroduplex joints, and the subsequent correction of some of these mismatched base pairs before replication. Observations on recA protein have provided information on parameters that affect the discrimination of relatedness from perfect or near-perfect homology and that affect the inclusion of mismatched base pairs in heteroduplex joints. The ability of recA protein to drive strand exchange past all single base-pair mismatches and to form extensively mismatched joints in superhelical DNA reflect its role in recombination and gene conversion. This error-prone process may also be related to its role in mutagenesis. RecA-mediated pairing reactions involving DNA of øX174 and G4, which are about 70 percent homologous, have yielded homologous recombinants (Cunningham et al. (1981) *Cell* 24: 213), although recA preferentially forms homologous joints between highly homologous sequences, and is implicated as mediating a homology search process between an invading DNA strand and a recipient DNA strand, producing relatively stable heteroduplexes at regions of high homology.

Therefore, is is preferred that targeting polynucleotides of the invention have homology clamps that are highly homologous to the predetermined target endogenous DNA sequence(s), most preferably isogenic. Typically, targeting polynucleotides of the invention have at least one homology clamp that is at least about 25 to 35 nucleotides long, and it is preferable that homology clamps are at least about 50 to 100 nucleotides long, and more preferably at least about 100–500 nucleotides long, although the degree of sequence homology between the homology clamp and the targeted sequence and the base composition of the targeted sequence will determine the optimal and minimal clamp lengths (e.g., G-C rich sequences are typically more thermodynamically stable and will generally require shorter clamp length). Therefore, both homology clamp length and the degree of sequence homology can only be determined with reference to a particular predetermined sequence, but homology clamps generally must be at least about 50 nucleotides long and must also substantially correspond or be substantially complementary to a predetermined target sequence. Preferably, a homology clamp is at least about 50 nucleotides long and is identical to or complementary to a predetermined target sequence. Without wishing to be bound by a particular theory, it is believed that the addition of recombinases to a targeting polynucleotide enhances the efficiency of homologous recombination between homologous, nonisogenic sequences (e.g., between an exon 2 sequence of a albumin gene of a Balb/c mouse and a homologous albumin gene exon 2 sequence of a C57/BL6 mouse), as well as between isogenic sequences.

The invention is preferably practiced with a complementary pair of targeting polynucleotides, usually of equal length, which are simultaneously or contemporaneously introduced into a eukaryotic cell harboring a predetermined endogenous target sequence, generally with at least one recombinase protein (e.g., recA). Under most circumstances, it is preferred that the targeting polynucleotides are incubated with recA or other recombinase prior to introduction into a eukaryotic cell, so that the recombinase protein(s) may be "loaded" onto the targeting polynucleotide(s). Incubation conditions for such recombinase loading are described infra, and also in U.S. Ser. No. 07/755,462, filed Sep. 4, 1991; U.S. Ser. No. 07/910,791, filed Jul. 9, 1992; and U.S. Ser. No. 07/520,321, filed May 7, 1990, each of which is incorporated herein by reference. A targeting polynucleotide may contain a sequence that enhances the loading process of a recombinase, for example a recA loading sequence is the recombinogenic nucleation sequence poly-[d(A–C)], and its complement, poly-[d (G–T)]. The duplex sequence poly[d (A–C)•(G–T)]$_n$, where n is from 5 to 25, is a middle repetitive element in eukaryotic DNA.

The invention may also be practiced with individual targeting polynucleotides which do not comprise part of a complementary pair. In each case, a targeting polynucleotide is introduced into a eukaryotic cell simultaneously or contemporaneously with a recombinase protein, typically in the form of a coated targeting polynucleotide (i.e., a polynucleotide preincubated with recombinase wherein the recombinase is noncovalently bound to the polynucleotide).

A targeting polynucleotide used in a method of the invention typically is a single-stranded nucleic acid, usually a DNA strand, or derived by denaturation of a duplex DNA, which is complementary to one (or both) strand(s) of the target duplex nucleic acid. The homology clamp sequence preferably contains at least 90–95% sequence homology with the target sequence, to insure sequence-specific targeting of the targeting polynucleotide to the endogenous DNA target. The single-stranded targeting polynucleotide is typically about 50–600 bases long, although a shorter or longer polynucleotide may also be employed. Alternatively, the targeting polynucleotide may be prepared in single-stranded form by oligonucleotide synthesis methods, which may first require, especially with larger targeting polynucleotides, formation of subfragments of the targeting polynucleotide, typically followed by splicing of the subfragments together, typically by enzymatic ligation.

Recombinase Proteins

Recombinases are proteins that, when included with an exogenous targeting polynucleotide, provide a measurable increase in the recombination frequency and/or localization frequency between the targeting polynucleotide and an endogenous predetermined DNA sequence. In the present invention, recombinase refers to a family of RecA-like recombination proteins all having essentially all or most of the same functions, particularly: (i) the recombinase protein's ability to properly bind to and position targeting polynucleotides on their homologous targets and (ii) the ability of recombinase protein/targeting polynucleotide complexes to efficiently find and bind to complementary endogenous sequences. The best characterized recA protein is from *E. coli*, in addition to the wild-type protein a number of mutant recA-like proteins have been identified (e.g., recA803). Further, many organisms have recA-like recombinases with strand-transfer activities (e.g., Fugisawa et al., (1985) *Nucl. Acids Res.* 13: 7473; Hsieh et al., (1986) *Cell* 44: 885; Hsieh et al., (1989) *J. Biol. Chem.* 264: 5089; Fishel et al., (1988) *Proc. Natl. Acad. Sci. USA* 85: 3683; Cassuto et al., (1987) *Mol. Gen. Genet.* 208: 10; Ganea et al., (1987) *Mol. Cell Biol.* 7: 3124; Moore et al., (1990) *J. Biol. Chem.* 19: 11108; Keene et al., (1984) *Nucl. Acids Res.* 12: 3057; Kimiec, (1984) *Cold Spring Harbor Symp.* 48:675; Kimeic, (1986) *Cell* 44: 545; Kolodner et al., (1987) *Proc. Natl. Acad. Sci. USA* 84 :5560; Sugino et al., (1985) *Proc. Natl. Acad, Sci. USA* 85: 3683; Halbrook et al., (1989) *J. Biol. Chem.* 264: 21403; Eisen et al., (1988) *Proc. Natl. Acad. Sci. USA* 85: 7481; McCarthy et al., (1988) *Proc. Natl. Acad. Sci. USA* 85: 5854; Lowenhaupt et al., (1989) *J. Biol. Chem.* 264: 20568, which are incorporated herein by reference. Examples of such recombinase proteins include, for example but not limitation: recA, recA803, uvsX, and other recA mutants and recA-like recombinases (Roca, A. I. (1990) *Crit. Rev. Biochem. Molec. Biol.* 25: 415), sep1 (Kolodner et al. (1987) *Proc. Natl. Acad. Sci. (U.S.A.)* 84: 5560; Tishkoff et al. *Molec. Cell. Biol.* 11: 2593), RuvC (Dunderdale et al. (1991) *Nature* 354: 506), DST2, KEM1, XRN1 (Dykstra et al. (1991) *Molec. Cell. Biol.* 11: 2583), STPα/DST1 (Clark et al. (1991) *Molec. Cell. Biol.* 11: 2576), HPP-1 (Moore et al. (1991) *Proc. Natl. Acad. Sci. (U.S.A.)* 88: 9067), other eukaryotic recombinases (Bishop et al. (1992) *Cell* 69: 439; Shinohara et al. (1992) *Cell* 69: 457); incorporated herein by reference. RecA may be purified from *E. coli* strains, such as *E. coli* strains JC12772 and JC15369 (available from A. J. Clark and M. Madiraju, University of California-Berkeley). These strains contain the recA coding sequences on a "runaway" replicating plasmid vector present at a high copy numbers per cell. The recA803 protein is a high-activity mutant of wild-type recA. The art teaches several examples of recombinase proteins, for example, from Drosophila, yeast, plant, human, and non-human mammalian cells, including proteins with biological properties similar to recA (i.e., recA-like recombinases).

Recombinase protein(s) (prokaryotic or eukaryotic) may be exogenously administered to a eukaryotic cell simultaneously or contemporaneously (i.e., within about a few hours) with the targeting polynucleotide(s). Such administration is typically done by microinjection, although electroporation, lipofection, and other transfection methods known in the art may also be used. Alternatively, recombinase proteins may be produced in vivo from a heterologous expression cassette in a transfected cell or transgenic cell, such as a transgenic totipotent embryonal stem cell (e.g., a murine ES cell such as AB-1) used to generate a transgenic non-human animal line or a pluripotent hematopoietic stem cell for reconstituting all or part of the hematopoietic stem cell population of an individual. Conveniently, a heterologous expression cassette includes a modulatable promoter, such as an ecdysone-inducible promoter-enhancer combination, an estrogen-induced promoter-enhancer combination, a CMV promoter-enhancer, an insulin gene promoter, or other cell-type specific, developmental stage-specific, hormone-inducible, or other modulatable promoter construct so that expression of at least one species of recombinase protein from the cassette can by modulated for transiently producing recombinase(s) in vivo simultaneous or contemporaneous with introduction of a targeting polynucleotide into the cell. When a hormone-inducible promoter-enhancer combination is used, the cell must have the required hormone receptor present, either naturally or as a consequence of expression a co-transfected expression vector encoding such receptor.

For making transgenic non-human animals (which include homologously targeted non-human animals) embryonal stem cells (ES cells) are preferred. Murine ES cells, such as AB-1 line grown on mitotically inactive SNL76/7 cell feeder layers (McMahon and Bradley, *Cell* 62:1073–1085 (1990)) essentially as described (Robertson, E. J. (1987) in *Teratocarcinomas and Embryonic Stem Cells: A Practical Approach*. E. J. Robertson, ed. (Oxford: IRL Press), p. 71–112) may be used for homologous gene targeting. Other suitable ES lines include, but are not limited to, the E14 line (Hooper et al. (1987) *Nature* 326: 292–295), the D3 line (Doetschman et al. (1985) *J. Embryol. Exp. Morph.* 87: 27–45), and the CCE line (Robertson et al. (1986) *Nature* 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal).

The pluripotence of any given ES cell line can vary with time in culture and the care with which it has been handled. The only definitive assay for pluripotence is to determine whether the specific population of ES cells to be used for targeting can give rise to chimeras capable of germline transmission of the ES genome. For this reason, prior to gene targeting, a portion of the parental population of AB-1 cells is injected into C57B1/6J blastocysts to ascertain whether the cells are capable of generating chimeric mice with extensive ES cell contribution and whether the majority of these chimeras can transmit the ES genome to progeny.

The vectors containing the DNA segments of interest can be transferred into the host cell by well-known methods, depending on the type of cellular host. For example, microinjection is commonly utilized for eukaryotic cells, although calcium phosphate treatment, electroporation, lipofection, biolistics or viral-based transfection also may be used. Other methods used to transform mammalian cells include the use of Polybrene, protoplast fusion, and others (see, generally, Sambrook et al. Molecular Cloning: A Laboratory Manual, 2d ed., 1989, Cold Spring Harbor Laboratory Press, Cold Spring Harbor, N.Y., which is incorporated herein by reference). Direct injection of DNA and/or recombinase-coated targeting polynucleotides into target cells, such as skeletal or muscle cells also may be used (Wolff et al. (1990) *Science* 247: 1465, which is incorporated herein by reference).

RecA protein is typically obtained from bacterial strains that overproduce the protein: wild-type *E. coli* recA protein and mutant recA803 protein may be purified from such strains. Alternatively, recA protein can also be purchased from, for example, Pharmacia (Piscataway, N.J.).

RecA protein forms a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any DNA molecule and can be formed in cells (e.g., mammalian cells), forming complexes with both single-stranded and double-stranded DNA.

Recombinase Coating of Targeting Polynucleotides

The conditions used to coat targeting polynucleotides with recA protein and ATPγS have been described in commonly assigned U.S. Ser. No. 07/910,791, filed Jul. 9, 1992; U.S. Ser. No. 07/755,462, filed Sep. 4, 1991; and U.S. Ser. No. 07/520,321, filed May 7, 1990, each incorporated herein by reference. Targeting polynucleotides can be coated using GTPγS, mixes of ATPγS with rATP and/or dATP, or dATP or rATP alone in the presence of an rATP generating system (Boehringer Mannheim). Various mixtures of GTPγS, ATPγS, ATP, ADP, dATP and/or rATP may be used, particularly preferred are mixes of ATPγS and ATP or ATPγS and ADP.

RecA protein coating of targeting polynucleotides is typically carried out as described in U.S. Ser. No. 07/910,791, filed Jul. 9, 1992 and U.S. Ser. No. 07/755,462, filed Sep. 4, 1991, which are incorporated herein by reference. Briefly, the targeting polynucleotide, whether double-stranded or single-stranded, is denatured by heating in an aqueous solution at 95–100° C. for five minutes, then placed in an ice bath for 20 seconds to about one minute followed by centrifugation at 0° C. for approximately 20 sec, before use. When denatured targeting polynucleotides are not placed in a freezer at −20° C. they are usually immediately added to standard recA coating reaction buffer containing ATPγS, at room temperature, and to this is added the recA protein. Alternatively, recA protein may be included with the buffer components and ATPγS before the polynucleotides are added.

RecA coating of targeting polynucleotide(s) is initiated by incubating polynucleotide-recA mixtures at 37° C. for 10–15 min. RecA protein concentration tested during reaction with polynucleotide varies depending upon polynucleotide size and the amount of added polynucleotide, and the ratio of recA molecule:nucleotide preferably ranges between about 3:1 and 1:3. When single-stranded polynucleotides are recA coated independently of their homologous polynucleotide strands, the mM and µM concentrations of ATPγS and recA, respectively, can be reduced to one-half those used with double-stranded targeting polynucleotides (i.e. recA and ATPγS concentration ratios are usually kept constant at a specific concentration of individual polynucleotide strand, depending on whether a single- or double-stranded polynucleotide is used).

RecA protein coating of targeting polynucleotides is normally carried out in a standard 1X RecA coating reaction buffer. 10X RecA reaction buffer (i.e., 10X AC buffer) consists of: 100 mM Tris acetate (pH 7.5 at 37° C.), 20 mM magnesium acetate, 500 mM sodium acetate, 10 mM DTT, and 50% glycerol). All of the targeting polynucleotides, whether double-stranded or single-stranded, typically are denatured before use by heating to 95–100° C. for five minutes, placed on ice for one minute, and subjected to centrifugation (10,000 rpm) at 0° C. for approximately 20 seconds (e.g., in a Tomy centrifuge). Denatured targeting polynucleotides usually are added immediately to room temperature RecA coating reaction buffer mixed with ATPγS and diluted with double-distilled $H_2O$, as necessary.

A reaction mixture typically contains the following components: (i) 2.4 mM ATPγS; and (ii) between 1–100 ng/µl of targeting polynucleotide. To this mixture is added about 1–20 µl of recA protein per 10–100 µl of reaction mixture, usually at about 5.2–11.0 mg/ml (purchased from Pharmacia or purified), and is rapidly added and mixed. The final reaction volume for RecA coating of targeting polynucleotide is usually in the range of about 10–500 µl. RecA coating of targeting polynucleotide is usually initiated by incubating targeting polynucleotide-RecA mixtures at 37° C. for about 10–15 min.

RecA protein concentrations in coating reactions varies depending upon targeting polynucleotide size and the amount of added targeting polynucleotide: recA protein concentrations are typically in the range of 5 to 50 µM. When single-stranded targeting polynucleotides are coated with recA, independently of their complementary strands, the concentrations of ATPγS and recA protein may optionally be reduced to about one-half of the concentrations used with double-stranded targeting polynucleotides of the same length: that is, the recA protein and ATPγS concentration ratios are generally kept constant for a given concentration of individual polynucleotide strands.

The coating of targeting polynucleotides with recA protein can be evaluated in a number of ways. First, protein binding to DNA can be examined using band-shift gel assays (McEntee et al., (1981) J. Biol. Chem. 256:8835). Labeled polynucleotides can be coated with recA protein in the presence of ATPγS and the products of the coating reactions may be separated by agarose gel electrophoresis. Following incubation of recA protein with denatured duplex DNAs the recA protein effectively coats single-stranded targeting polynucleotides derived from denaturing a duplex DNA. As the ratio of recA protein monomers to nucleotides in the targeting polynucleotide increases from 0, 1:27, 1:2.7 to 3.7:1 for 121-mer and 0, 1:22, 1:2.2 to 4.5:1 for 159-mer, targeting polynucleotide's electrophoretic mobility decreases, i.e., is retarded, due to recA-binding to the targeting polynucleotide. Retardation of the coated polynucleotide's mobility reflects the saturation of targeting polynucleotide with recA protein. An excess of recA monomers to DNA nucleotides is required for efficient recA coating of short targeting polynucleotides (Leahy et al., (1986) J. Biol. Chem. 261:6954).

A second method for evaluating protein binding to DNA is in the use of nitrocellulose fiber binding assays (Leahy et al., (1986) J. Biol. Chem. 261:6954; Woodbury, et al., (1983) Biochemistry 22(20):4730–4737. The nitrocellulose filter binding method is particularly useful in determining the dissociation-rates for protein:DNA conplexes using labeled DNA. In the filter binding assay, DNA:protein complexes are retained on a filter while free DNA passes through the filter. This assay method is more quantitative for dissociation-rate determinations because the separation of DNA:protein complexes from free targeting polynucleotide is very rapid.

Cell-Uptake Components

A targeting polynucleotide of the invention may optionally be conjugated, typically by noncovalent binding, to a cell-uptake component. Various methods have been described in the art for targeting DNA to specific cell types. A targeting polynucleotide of the invention can be conjugated to essentially any of several cell-uptake components known in the art. For targeting to hepatocytes, a targeting polynucleotide can be conjugated to an asialoorosomucoid (ASOR)-poly-L-lysine conjugate by methods described in the art and incorporated herein by reference (Wu GY and Wu CH (1987) J. Biol. Chem. 262: 4429; Wu GY and Wu CH (1988) *Biochemistry* 27: 887; Wu GY and Wu CH (1988) *J. Biol. Chem.* 263: 14621; Wu GY and Wu CH (1992) *J. Biol. Chem.* 267: 12436; Wu et al. (1991) *J. Biol. Chem.* 266: 14338; and Wilson et al. (1992) *J. Biol. Chem.* 267: 963, WO92/06180; WO92/05250; and WO91/17761 which are incorporated herein by reference).

Alternatively, a cell-uptake component may be formed by incubating the targeting polynucleotide with at least one lipid species and at least one protein species to form protein-lipid-polynucleotide complexes consisting essentially of the targeting polynucleotide and the lipid-protein cell-uptake component. Lipid vesicles made according to Felgner (WO91/17424, incorporated herein by reference) and/or cationic lipidization (WO91/16024, incorporated herein by reference) or other forms for polynucleotide administration (EP 465,529, incorporated herein by reference) may also be employed as cell-uptake components.

Typically, a targeting polynucleotide of the invention is coated with at least one recombinase and is conjugated to a cell-uptake component, and the resulting cell targeting complex is contacted with a target cell under uptake conditions (e.g., physiological conditions) so that the targeting polynucleotide and the recombinase(s) are internalized in the target cell. A targeting polynucleotide may be contacted simultaneously or sequentially with a cell-uptake component and also with a recombinase; preferably the targeting polynucleotide is contacted first with a recombinase, or with a mixture comprising both a cell-uptake component and a recombinase under conditions whereby, on average, at least about one molecule of recombinase is noncovalently attached per targeting polynucleotide molecule and at least about one cell-uptake component also is noncovalently attached. Most preferably, coating of both recombinase and cell-uptake component saturates essentially all of the available binding sites on the targeting polynucleotide. A targeting polynucleotide may be preferentially coated with a cell-uptake component so that the resultant targeting complex comprises, on a molar basis, more cell-uptake component than recombinase(s). Alternatively, a targeting polynucleotide may be preferentially coated with recombinase(s) so that the resultant targeting complex comprises, on a molar basis, more recombinase(s) than cell-uptake component.

Cell-uptake components are included with recombinase-coated targeting polynucleotides of the invention to enhance the uptake of the recombinase-coated targeting polynucleotide(s) into cells, particularly for in vivo gene targeting applications, such as gene therapy to treat genetic diseases, including neoplasia, and targeted homologous recombination to treat viral infections wherein a viral sequence (e.g., an integrated hepatitis B virus (HBV) genome or genome fragment) may be targeted by homologous sequence targeting and inactivated. Alternatively, a targeting polynucleotide may be coated with the cell-uptake component and targeted to cells with a contemporaneous or simultaneous administration of a recombinase (e.g., liposomes or immunoliposomes containing a recombinase, a viral-based vector encoding and expressing a recombinase).

Several disease states may be amenable to treatment or prophylaxis by targeted alteration of heptocytes in vivo by homologous gene targeting. For example and not for limitation, the following diseases, among others not listed, are expected to be amenable to targeted gene therapy: hepatocellular carcinoma, HBV infection, familial hypercholesterolemia (LDL receptor defect), alcohol sensitivity (alcohol dehydrogenase and/or aldehyde dehydrogenase insufficiency), hepatoblastoma, Wilson's disease, congenital hepatic porphyrias, and inherited disorders of hepatic metabolism. Where targeting of hepatic cells in vivo is desired, a cell-uptake component consisting essentially of an asialoglycoprotein-poly-L-lysine conjugate is preferred. The targeting complexes of the invention which may be used to target hepatocytes in vivo take advantage of the significantly increased targeting efficiency produced by association of a targeting polynucleotide with a recombinase which, when combined with a cell-targeting method such as that of WO92/05250 and/or Wilson et al. (1992) *J. Biol. Chem.* 267: 963, provide a highly efficient method for performing in vivo homologous sequence targeting in cells, such as hepatocytes.

For many types of in vivo gene therapy to be effective, a significant number of cells must be correctly targeted, with a minimum number of cells having an incorrectly targeted recombination event. To accomplish this objective, the combination of: (1) a targeting polynucleotide(s), (2) a recombinase (to provide enhanced efficiency and specificity of correct homologous sequence targeting), and (3) a cell-uptake component (to provide enhanced cellular uptake of the targeting poynucleotide), provides a means for the efficient and specific targeting of cells in vivo, making in vivo homologous sequence targeting, and gene therapy, practicable.

Targeting of Endogenous DNA Sequences In Vivo

Generally, any predetermined endogenous DNA sequence can be altered by homologous recombination (which includes gene conversion) with an exogenous targeting polynucleotide (or complementary pair of targeting polynucleotides) that has at least one homology clamp which substantially corresponds to or is substantially complementary to a predetermined endogenous DNA target sequence and which is introduced with a recombinase (e.g., recA) into a eukaryotic cell having the predetermined endogenous DNA sequence. Typically, a targeting polynucleotide (or complementary polynucleotide pair) has a portion having a sequence that is not present in the preselected endogenous targeted sequence(s) (i.e., a nonhomologous portion) which may be as small as a single mismatched nucleotide or may span up to about several kilobases or more of nonhomologous sequence. Generally, such nonhomologous portions are flanked on each side by homology clamps, although a single flanking homology clamp may be used. Nonhomologous portions are used to make insertions, deletions, and/or replacements in a predetermined endogenous targeted DNA sequence, and/or to make single or multiple nucleotide substitutions in a predetermined endogenous target DNA sequence so that the resultant recombined sequence (i.e., a targeted recombinant endogenous sequence) incorporates some or all of the sequence information of the nonhomologous portion of the targeting polynucleotide(s). Additions and deletions may be as small as 1 nucleotide or may range up to about 2 to 10 kilobases or more.

In one application, a targeting polynucleotide can be used to repair a mutated sequence of a structural gene by replacing it or converting it to a wild-type sequence (e.g., a sequence encoding a protein with a wild-type biological activity). For example, such applications could be used to convert a sickle cell trait allele of a hemoglobin gene to an allele which encodes a hemoglobin molecule that is not susceptible to sickling, by altering the nucleotide sequence encoding the β-subunit of hemoglobin so that the codon at position 6 of the β subunit is converted Valβ6—>Gluβ6 (Shesely et al. (1991) op.cit.). Other genetic diseases can be corrected, either partially or totally, by replacing, inserting, and/or deleting sequence information in a disease allele using appropriately selected exogenous targeting polynucleotides. For example but not for limitation, the ΔF508 deletion in the human CFTR gene can be corrected by targeted homologous recombination employing a recA-coated targeting polynucleotide of the invention.

Gene Inactivation

In addition to correcting disease alleles, exogenous targeting polynucleotides can be used to inactivate one or more genes in a cell (or transgenic nonhuman animal).

Once the specific target genes to be modified are selected, their sequences will be scanned for possible disruption sites (convenient restriction sites, for example). Plasmids are engineered to contain an appropriately sized gene sequence with a deletion or insertion in the gene of interest and at least one flanking homology clamp which substantially corresponds or is substantially complementary to an endogenous target DNA sequence. Vectors containing a targeting polynucleotide sequence are typically grown in E. coli and then isolated using standard molecular biology methods, or may be synthesized as oligonucleotides. Direct targeted inactivation which does not require vectors may also be done. When using microinjection procedures it may be preferable to use a transfection technique with linearized sequences containing only modified target gene sequence and without vector or selectable sequences. The modified gene site is such that a homologous recombinant between the exogenous targeting polynucleotide and the endogenous DNA target sequence can be identified by using carefully chosen primers and PCR, followed by analysis to detect if PCR products specific to the desired targeted event are present (Erlich et al., (1991) Science 252: 1643, which is incorporated herein by reference). Several studies have already used PCR to successfully identify and then clone the desired transfected cell lines (Zimmer and Gruss, (1989) Nature 338:150; Mouellic et al., (1990) Proc. Natl. Acad. Sci. USA 87:4712; Shesely et al., (1991) Proc. Natl. Acad. Sci. USA 88:4294, which are incorporated herein by reference). This approach is very effective when the number of cells receiving exogenous targeting polynucleotide(s) is high (i.e., with microinjection, or with liposomes) and the treated cell populations are allowed to expand to cell groups of approximately $1 \times 10^4$ cells (Capecchi, (1989) Science 244:1288). When the target gene is not on a sex chromosome, or the cells are derived from a female, both alleles of a gene can be targeted by sequential inactivation (Mortensen et al., (1991) Proc. Natl. Acad. Sci. USA 88:7036).

Homologous Pairing of Targeting Polynucleotides Having Chemical Substituents

Exogenous targeting polynucleotides that have been modified with appended chemical substituents may be introduced along with recombinase (e.g., recA) into a metabolically active eukaryotic cell to homologously pair with a predetermined endogenous DNA target sequence in the cell. Typically such exogenous targeting polynucleotides are derivatized, and additional chemical substituents are attached, either during or after polynucleotide synthesis, respectively, and are thus localized to a specific endogenous target sequence where they produce an alteration or chemical modification to a local DNA sequence. Preferred attached chemical substituents include: cross-linking agents, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, base-modification agents, immunoglobulin chains, and oligonucleotides. Iron/EDTA chelates are particularly preferred chemical substituents where local cleavage of a DNA sequence is desired (Hertzberg et al. (1982) J. Am. Chem. Soc. 104: 313; Hertzberg and Dervan (1984) Biochemistry 23: 3934; Taylor et al. (1984) Tetrahedron 40: 457; Dervan, PB (1986) Science 232: 464, which are incorporated herein by reference). Preferred attachment chemistries include: direct linkage, e.g., via an appended reactive amino group (Corey and Schultz (1988) Science 238: 1401, which is incorporated herein by reference) and other direct linkage chemistries, although streptavidin/biotin and digoxigenin/anti-digoxigenin antibody linkage methods may also be used. Methods for linking chemical substitutents are provided in U.S. Pat. Nos. 5,135,720, 5,093,245, and 5,055,556, which are incorporated herein by reference. Other linkage chemistries may be used at the discretion of the practitioner.

The broad scope of this invention is best understood with reference to the following examples, which are not intended to limit the invention in any manner.

EXPERIMENTAL EXAMPLES

Example 1

Homologous Targeting of recA-Coated Chemically-Modified Polynucleotides in Cells Homologously targeted exogenous targeting polynuclotides specifically target human DNA sequences in intact nuclei of metabolically active cells. RecA-coated complementary exogenous targeting polynucleotides were introduced into metabolically active human cells encapsulated in agarose microbeads and permeabilized to permit entry of DNA/protein complexes using the Jackson-Cook method (Cook, P. R. (1984) EMBO J. 3: 1837; Jackson and Cook (1985) EMBO J. 4: 919; Jackson and Cook (1985) EMBO J. 4: 913; Jackson and Cook (1986) J. Mol. Biol. 192: 65; Jackson et al. (1988) J. Cell. Sci. 90: 365, which are incorporated herein by reference). These experiments were designed to specifically target homologous DNA sequences with recA protein in intact nuclei of metabolically active human HEp-2 cells.

Jackson and Cook previously demonstrated that the nuclear membranes of human or other cells may be permeabilized without loss of metabolic function if the cells are first encapsulated in a gel of agarose microbeads. The agarose microbead coat contains the cell constituents and preserves native conformation of chromososomal DNA, while permitting diffusion of macromolecules into and out of the cell compartment. Wittig et al.(1991) Proc. Natl. Acad. Sci. (U.S.A.) 88: 2259, which is incorporated herein by reference, demonstrated that monoclonal antibodies directed against left-handed Z-DNA could be diffused into these agarose-embedded cells, and that the antibodies were specifically targeted to chromosomal sequences and conformations. In a similar manner, we incubated biotin- or FITC-labeled complementary DNA targeting polynucleotides coated with recA with agarose-coated cell nuclei and verified the correct homologous targeting of the exogenous targeting polynucleotides to specific predetermined human DNA sequences in cell nuclei of metabolically active cells.

RecA-mediated homologous gene targeting with complementary oligonucleotides in intact human cell nuclei was verified directly by homologous targeting using targeting polynucleotides that were biotinylated. These were subsequently labeled with a fluorescent compound to verify homologous pairing at specific locations having the predetermined sequence(s). RecA-coated targeting polynucleotides for human chromosome 1 pericentrometric alpha-satellite DNA sequences were specifically targeted to chromosome 1 centromere sequences in living human cell nuclei that were permeabilized and suspended in agarose.

In these experiments, recA-coated biotinylated exogenous targeting polynucleotides containing homologous sequences to human chromosome 1 alpha satellite DNA were incubated with human HEp-2 cells. The cells were embedded in agarose, then treated with standard buffers (according to Jackson and Cook, op.cit.) to remove the cytoplasmic membrane and cytoplasm immediately before the addition of targeting polynucleotide coated with recA protein.

The experiments were performed with the following results.

First, in order to test protocols to be used in nuclear encapsulation, freshly trypsinized growing human HEp-2 tumor cells were suspended in complete DMEM encapsulated in a mixture of agarose (2.5%, Fisher-Bioteck) and complete DMEM media adapting the protocols of Nilsson et al., 1983, so that the final agarose concentration was 0.5% (4 volumes cells in suspension with 1 volume 2.5% agarose), and the final cell concentration range was approximately $2.4 \times 10^7$ to $8 \times 10^5$. The encapsulated cells in agarose "beads" were placed in petri dishes to which DMEM complete media was added and were allowed to grow for 24 hr in an incubator at 37° C., 7% $CO_2$. At 24 hr, the cells were clearly growing and multiplying and thus were alive and metabolically active.

An aliquot of agarose containing cells (in beads in DMEM medium) was treated to remove the cytoplasmic membrane and cytoplasm by addition of ice-cold sterile PBS, New Buffer (Jackson et al. (1988) op.cit.: 130 mM KCl, 10 mM $Na_2HPO_4$, 1 mM $MgCl_2$, 1 mM $Na_2ATP$, and 1 mM dithithreitol, pH 7.4 ), New Buffer with 0.5% Triton-X 100, New Buffer with 0.2% BSA, then was centrifuged at low speed using protocols developed by Jackson and Cook, 1985 and 1986 op.cit.; Wittig et al. (1989) *J. Cell. Biol.* 108: 755; Wittig et al. (1991) op.cit.) who have shown that this treatment allows the nuclear membrane to remain morphologically intact. The nuclei are metabolically active as shown by a DNA synthesis rate of 85 to 90% compared with that of untreated control cells.

Cytoplasm was effectively removed by the above treatment, and the encapsulated nuclei were intact as demonstrated by their morphology and exclusion of 0.4% trypan blue. Nuclei in agarose were returned to the humidified $CO_2$ incubator at 37° C. for 24 hr and remained metabolically active. We observed that filtered, sterile mineral oil used in the emulsification process was difficult to remove entirely and interfered with the microscopic visualization of suspended nuclei. Therefore, the cell-agarose suspension process was simplified. In subsequent experiments cells were gently vortexed with melted (39° C.) agarose, then the agarose-cell mixture was sterilely minced before New Buffer treatments. This simpler process, eliminating the oil step, makes it easier to visualize the cells and chromosomes at the completion of reactions.

After mincing of the agar and New Buffer treatments of the cells, the above protocols were used to homologously target endogenous DNA sequences in encapsulated nuclei as follows: 16.5 µl recA-coated (or non-recA-coated control) nick-translated DNA (labeled with biotin-14-dATP) targeting polynucleotide was prepared and bound under standard native recA protocols (see U.S. Ser. No. 07/755,462 and 07/910,791). Minced agarose fragments were centrifuged and New Buffer supernatant removed. The fragments were resuspended in 1 X AC buffer in a 1.5-ml Eppendorf tube, then centrifuged for removal of the buffer (leaving an estimated 50 to 75 µl of buffer), and prepared targeting polynucleotide was mixed with the fragments of agarose-containing nuclei. Reactions were incubated in a 37° C. water bath for 2 to 4 hr, then washed, incubated in standard preblock solution, then in preblock supplement with 10 µg/ml FITC-avidin (Vector, DCS grade), and again washed. Experimental results were analyzed by placing a minute amount of a reaction with 3 to 4 µl antifade on a slide with a slide cover and viewing it by using the Zeiss CLSM-10 confocal laser scanning microscope (CLSM). Completed reactions were also stored refrigerated for later examination.

In the first in vivo experiment, metabolically active HEp-2 cells suspended in 1×PBS were encapsulated in agarose by gentle vortexing, treated using New Buffer protocols, then incubated for 3 hr 15 min with 100 ng of recA-coated targeting polynucleotide specific for Chromosome 1 alpha-satellite DNA biotinylated with bio-14-dATP by nick translation (BRL, Nick Translation System) using pUC 1.77 plasmid DNA (a 1.77 kb long EcoRI fragment of human DNA in the vector pUC9; Cooke et al. (1979) *Nucleic Acids Res.* 6: 3177; Emmerich et al. (1989) *Exp. Cell. Res.* 181: 126). We observed specific targeting by the alpha-satellite targeting polynucleotide to pericentromeric chromosome 1 targets in intact nuclei of metabolically active cells. The signals were essentially identical to those using the same targeting polynucleotide with methanol (or ethanol)-fixed HEp-2 cell targets in suspension. FIGS. 1 and 2 show specific targeting signals in several metabolically active cells from this experiment.

In the second in vivo experiment, cells suspended in incomplete DMEM media instead of 1×PBS were encapsulated in agarose and treated with 62.5 ng of the same targeting polynucleotide used in the first experiment described above and 62.5 ng of a freshly biotinylated targeting polynucleotide prepared under the same protocols. In this experiment, the minced agarose fragments were not resuspended in 1×AC buffer before addition of targeting polynucleotide and some nuclei disintegrated, especially with subsequent centrifugation. The results show that in the nuclei that remained intact, the targeting polynucleotides coated with recA specifically targeted predetermined human DNA targets. In contrast, targeting polynucleotides in reactions without recA did not correctly target the predetermined human DNA sequences. When the targeted DNA (generated from the recA-coated targeting polynucleotides) was decondensed from the nuclei, the alpha-satellite repeat sequences showed precise and evenly spaced signals along the "string" of the alphoid satellite DNA sequences.

Thus, the recA-coated targeting polynucleotides were targeted to the repetitive alpha satellite sequences of Chromosome 1. This result showed DNA targeting in intact nuclei to specific human Chromosome 1 sequences. An example of the experimentally extended DNA with specific alpha-satellite signals appears in FIG. 3.

In the third experiment, cells were suspended in 1×PBS or in incomplete DMEM media before vortexing with agarose and were tested using 62.5 ng of targeting polynucleotide in reactions with and without recA protein. In addition, the reactions were divided in half and washed and FITC-avidin treated in either buffer adjusted to pH 7 or pH 7.4. Cells were incubated with the recA coated targeting polynucleotide for 3 hr 25 min. Live nuclei treated with targeting polynucleotide alone without recA showed no signals. In the recA-treated reactions, relatively weaker signals were observed in nuclei incubated in 1×PBS, whereas very strong specific signals were present in nuclei that had been incubated in incomplete DMEM. There was clearly significantly more signal present in nuclei that were washed and treated with FITC-avidin at pH 7.4 compared with nuclei incubated at pH 7.0. FIG. 4 shows nuclei that were treated with recA coated targeting polynucleotides and incubated at both pH 7.4 and 7.0.

In a fourth experiment, HEp-2 cells were embedded in agarose prepared with 1×PBS, New Buffer treated, then treated with 100 ng of biotinylated targeting polynucleotide complementary to Chromosome 1 alpha-satellite DNA. Controls in this experiment also included reactions without recA protein and additional control reactions supplemented with an identical amount of BSA protein to replace the recA protein. Additionally, cells were also embedded in agarose prepared with 1×AC buffer. Examples of specific targeting to endogenous target sequences were recorded.

In a fourth experiment, we directly determined if the embedded nuclei under the conditions used above were metabolically active. The nuclei in agarose were incubated with bio-21-rUTP in complete medium, then incubated for 2 days in the humidified $CO_2$ atmosphere. After 2 days at 37° C., the cells were examined. Bio-21-rUTP was incorporated in RNA and incubated with FITC-streptavidin. FITC was specifically associated with nucleoli indicative of ribosomal RNA biosynthesis, thus directly showing metabolic activity in these human cells. Similar results were obtained using DNA precursors to measure DNA synthesis. In this experiment it was clear that the majority of nuclei in the PBS agarose reaction had condensed chromosomes. There was nuclear division in a number of these nuclei also, indicative of full metabolic viability, which was also shown in the AC buffer-treated cells.

A fifth experiment was performed using, again, HEp-2 cells embedded in agarose. Final concentration of the cells in agarose was $3.7 \times 10^6$/ml. The cells were suspended in 1×PBS prior to combining with agarose. The final agarose concentration was 0.5%. There were two reactions, one in which recA was used to coat targeting polynucleotide, the second in which recA protein was replaced by BSA at the same protein concentration followed by New Buffer treatments to remove the cytoplasm. The nuclei in agarose were incubated for 3 hr with targeting polynucleotide, then processed for detection of correctly targeted polynucleotide using the protocols describe previously. FITC-avidin was used to visualize the biotinylated targeting polynucleotide at a concentration of 20 µg/ml. Results showed that cells with the recA-coated complementary targeting polynucleotide displayed specific signals in 25% or more of the intact nuclei. In contrast, the BSA-treated controls did not show any signal.

Cells in agarose from this experiment were further incubated at 37° C. in the $CO_2$ incubator in complete medium. At 22 hr, these cells were metabolically active. Chromosomes were condensed, and a number of nuclei were in the process of dividing. In these experiments, a significant number of the cells incubated with recA-coated complementary targeting polynucleotides showed specific signal, whereas 0% of the cells incubated with targeting polynucleotide alone showed specific signal.

In summary, recA-coated biotinylated targeting polynucleotides for human chromosome 1 alpha-satellite DNA were specifically targeted to human HEp-2 epithelial carcinoma chromosomal DNA in intact cell nuclei of metabolically active cells that had been suspended in agarose, then treated with buffers and recA-coated targeting polynucleotides under suitable reaction conditions (supra and U.S. Ser. No. 07/755,462; U.S. Ser. No. 07/755,462; and U.S. Ser. No. 07/520,321, incorporated herein by reference). Specific binding by the recA-coated targeting polynucleotide to chromatin alpha-satellite DNA was observed only in the agarose embedded nuclei which were incubated with recA-coated targeting polynucleotides. Control nuclei incubated with targeting polynucleotides in the absence of recA and/or with nonspecific protein exhibited no signal.

Targeting of Human p53 Gene

We performed recA-mediated homologous targeting of biotinylated targeting polynucleotides that were homologous to the human p53 tumor supressor gene, and compared the results to targeting of alpha satellite DNA sequences in human chromosome 1. In these experiments, exponentially growing cells were trypsinized, washed, suspended in incomplete medium and encapsulated in agarose. The agarose was minced into pieces with a razor blade and the encapsulated cells were treated with New Buffer. A sample from each group was removed to verify that nuclei were intact.

Nuclei were washed in 1××AC buffer and incubated with recA-coated complementary single-stranded DNA oligonucleotides (i.e., exogenous targeting polynucleotides) for 3.5 hours at 37° C. The alpha satellite DNA targeting polynucleotides for chromosome 1 were previously described and were nick-translated with biotinylated deoxyribonucleotides (bio-14-dATP). The p53 tumor suppressor gene polynucleotide was obtained from Oncor (209 Perry Parkway, Gaithersburg, Md. 20877) and is a 1.2 kilobase cDNA fragment from a wild-type human p53 gene (Fields and Jang, (1990) *Science* 242: 1046; Miller et al. (1986) *Nature* 319: 783; Zakut-Houre et al. (1985) *EMBO J.* 4: 1251). The 1.2 kilobase human p53 DNA was nick-translated with biotinylated deoxyribonucleotides and yielded a population of biotinylated targeting polynucleotides having a size range (about 100 to 600 nucleotides) similar to that obtained for the human chromosome 1 alpha satellite targeting polynucleotides. The targeting polynucleotides were separately incubated with encapsulated cells. Following incubation 3 washes of 1.75×SSC were done, and sampled nuclei were verified as intact after the washing step. After washing, the targeted encapsulated cell nuclei were incubated in preblock and FITC-avidin was added to preblock buffer to a final concentration of 20 µg/ml for 15 minutes in the dark. The targeted encapsulated cell nuclei were washed sequentially in 4×SSC, 4×SSC with 0.1% Triton X-100, and then 4×SSC. Samples of nuclei were again taken and used to verify that the targeted nuclei were metabolically active. Microscopic examination showed that metabolically active cells contained specific FITC-targeting polynucleotide:targeted endogenous sequence complexes (shown in FIG. 5). The p53 targeting polynucleotides were specifically targeted to human chromosome 17, the location of the endogenous human p53 gene sequences, indicating specific pairing of a targeting polynucleotide to a unique endogenous DNA target sequence. The human chromosome 1 alpha satellite DNA was also specifically targeted to the chromosome 1 pericentromeric satellite sequences.

The experiments validated a highly specific DNA targeting technique for human or other cells as evidenced by homologous sequence targeting techniques in metabolically active cells. The targeting technique employs the unique properties of recA-mediated DNA sequence targeting with single-stranded (complementary) short targeting polynucleotides. Native intact nuclei were incubated with labeled, heat-denatured targeting polynucleotides coated with recA protein. The DNA hybridized to the predetermined targeted homologous sequences. In these experiments, the targeting polynucleotides formed paired complexes with specific gene sequences within metabolically active cell nuclei. This in vivo targeting by recA-mediated homologous targeting polynucleotides shows the targeting specificity and therapeutic potential for this new in vivo methodology. Application of recA or other recombinase-mediated targeting of (complementary) ssDNA or denatured dsDNA targeting polynucleotides to predetermined endogenous DNA targets is important for human gene entry, gene knockout, gene replacement, and gene mutation or correction.

Example 2

Correcting a Mutant Gene to Produce a Functional Gene Product

Homologously targeted complementary DNA oligonucleotides were used to correct 11 bp insertion mutations in vector genes and restore vector gene expression and vector protein function in microinjected mammalian cells.

Experiments were designed to test whether homologously targeted complementary 276-bp oligonucleotide targeting polynucleotides could correct an 11-bp insertion mutation in the lacZ gene of a mammalian DNA vector which encoded a nonfunctional β-galactosidase, so that a corrected lacZ gene encoded and expressed a functional enzyme. Functional enzyme (β-galactosidase) was detected by an X-gal assay that turns cells expressing a revertant (i.e., corrected) lacZ gene a blue color.

NIH3T3 cells microinjected with the mutant test vector bearing an 11 basepair insertion in the lacZ coding sequence do not produce any detectable functional β-galactosidase enzyme. In contrast, cells microinjected with the wild type test vector do produce functional enzyme.

We obtained the functional lac plasmid pMC1lacpA for use as a positive control for expression of β-galactosidase. pMC1lacXpA is the target test mutant plasmid (shown in FIG. 6). It is identical to pMC1lacpA (shown in FIG. 7) but has a 11-bp XbaI linker insertional mutation. This plasmid does not express β-galactosidase activity in mouse NIH3T3 cells when introduced by electroporation. It does not produce blue color in the presence of X-GAL indicative of β-galactosidase production following vector microinjection. Negative controls with mock or noninjected cells we also done. Using these controls and NIH3T3 cells have no detectable background blue staining.

The plasmid pMC1lacpA (8.4 kb) contains the strong polyoma virus promoter of transcription plus ATG placed in front of the lacZ gene. The polyadenylation signal from SV40 virus was placed in back of the lacZ gene. The plasmid vector was pIB130 (shown in FIG. 8) from IBI (New Haven, Conn.). The mutant vector pMC1lacpA has a 11-bp insertion in the XbaI site. This mutation consists of the inserted sequence CTCTAGACGCG (see FIG. 9).

In several control microinjection experiments using pMC1lacXpA we consistently failed to detect any blue microinjected cells. In contrast, in various experiments approximately 8 to 13% of the 3T3 cells injected with pMC1lacpA DNA expressed β-galactosidase as evidenced by their blue color. No cells microinjected with injection buffer alone or mock injected were observed as blue.

We synthesized two 20-bp primers for producing a 276-bp PCR product (see FIG. 9) from the wild-type lacZ sequence for use as targeting polynucleotides. We chose this 276-bp fragment to span the 11 bp insertion mutation as a nonhomologous sequence. The 276-bp DNA oligonucleotide was separated by gel electrophoresis and electroeluted from agarose, ethanol precipitated, and its concentration determined by absorbance at 260 nm. The 276-bp fragment was 5' end-labeled with $^{32}P$ and specifically D-looped with the pMC1lacXpA or pMC1lacpA plasmid DNA using recA as shown by agarose gel electrophoresis.

Experiments were designed to test for β-galactoside production in cells microinjected with pMC1lacXpA vectors with targeting polynucleotide-target complexes using complementary 276-bp oligonucleotide targeting polynucleotide treated with recA. The 276-mer targeting polynucleotides in 1 X TE buffer were denatured by heating at 100° C. for 5 min and immediately quenched in an ice bath for 1 min. The DNA solution was collected at 4° C. by centrifugation. RecA-mediated targeting polynucleotide reactions containing a final volume of 10 μl were assembled using 1.0 μl 10xx/AC buffer, 1.5 μl 16 mM ATPγS, 3.8 μl dd H$_2$O, 1.2 μl recA protein solution (13 μg/μl), and 2.5 μl of a 30 μg/ml stock of heat-denatured 276-bp targeting polynucleotide. The recA protein was allowed to coat the DNA for 10 min at 37° C. Next, 1.0 μl of 10xAC buffer, 1.0 μl of 0.2 M magnesium acetate, 1.3 μl of pMC1lacXpA (1.0 μg/μl), and 6.7 μl of dd H$_2$O was added to a final volume of 20 μl. Control reactions were performed without added recA protein.

NIH3T3 cells were capillary needle microinjected with targeting polynucleotide-target DNA mixtures loaded in glass pipettes freshly pulled into microneedles using a Sutter instruments microprocessor controlled apparatus. An ECET Eppendorf microinjection pump and computerized micromanipulator were used for computer-assisted microinjection using an Olympus IMT-2 inverted microscope. Cells were carefully microinjected under controlled pressure and time. NIH3T3 cells injected with pMC1lacpA showed approximately 9% of the injected cells were blue. None (0%) of the cells injected with pMC1lacXpA DNA in reactions containing the 276 bp oligonucleotide but without recA protein showed a blue color. In marked contrast, approximately 1% of the cells microinjected with the recA-mediated 276-bp targeting polynucleotide targeted to the pMC1lacXpA target hybrid were blue. Thus, these measurements indicate that the mutant pMC1lacXpA gene can be targeted and corrected by the 276-bp oligonucleotide, which has been targeted with recA-coated targeting polynucleotides. In summary, these measurements show that the 11 bp Xba I insertion mutation can be corrected with the recA-mediated targeted corrected in vivo, but not with the 276-bp oligonucleotide alone. Note that the in situ identification of 3T3 cells expressing β-galactosidase was performed following incubation with X-gal (5-bromo-4-chloro-3-indolyl-β- galactopyranoside) (Sigma), as described by Fischer et al. (1988) *Nature* 332: 853; Price et al. (1987) *Proc. Natl. Acad. SCi. (U.S.A.)* 84: 156; Lim and Chae (1989) *Biotechniques* 7: 576.

Example 3

Correcting a Human CFTR Disease Allele

Homologously targeted complementary DNA oligonucleotides were used to correct a naturally occurring 3 bp deletion mutation in a human CFTR allele and restore expression of a functional CFTR protein in targeted mammalian cells.

A major goal of cystic fibrosis (CF) gene therapy is the correction of mutant portions of the CF transmembrane conductance regulator (CFTR) gene by replacement with wild-type DNA sequences to restore the normal CFTR protein and ion transport function. Targeting polynucleotides that were coated with recA protein were introduced into transformed CF airway epithelial cells, homozygous for both alleles ΔF508 CFTR gene mutation, by either intranuclear microinjection, electroporation, or by transfection with a protein-DNA-lipid complex.

Isolation and characterization of the CFTR gene (Rommens et al. (1989) *Science* 245: 1059; Riordan et al. (1989) *Science* 245: 1066, incorporated herein by reference) has been crucial for understanding the biochemical mechanism(s) underlying CF pathology. The most common mutation associated with CF, a 3-base-pair, in-frame deletion eliminating a phenylalanine at amino acid position 508 (ΔF508) of CFTR, has been found in about 70% of all CF chromosomes (Kerem et al. (1989) *Science* 245: 1073; Kerem et al. (1990) *Proc. Natl. Acad. Sci. (U.S.A.)* 87: 8447). Correction of ΔF508 and other CFTR DNA mutations lies at the basis of DNA gene therapy for CF disease. Elimination of the cAMP-dependent Cl ion transport defect associated with CFTR gene mutations has been accomplished through the introduction of the transcribed portion of wild-type CFTR cDNA into CF epithelial cells (Rich et al. (1990) *Nature* 347: 358; Drumm et al. (1990) *Cell* 62: 1227).

An immortalized CF tracheobronchial epithelial human cell line, ΣCFTE29o-, is homozygous for the ΔF508 mutation (Kunzelmann et al. (1992) *Am. J. Respir. Cell. Mol. Biol.*, in press). These cells are useful as targets for homologous recombination analysis, because they contain the same 3 basepair deletion in CFTR allele on all copies of chromosome 7. Replacement of the ΔF508 allele with wild-type CFTR DNA is indicated only when homologous recombination has occurred. The 491 bp region of the CFTR gene spanning exon 11 and containing 3' and 5' flanking intron sequences was selected from sequence data published previously (Zielenski et al. (1991) *Genomics* 10: 214, incorporated herein by reference) and used as a targeting polynucleotide. The DNA fragment was PCR amplified in preparative quantities and then denatured for introduction into cells as recA-coated complementary ssDNA (or dsDNA). Exponentially growing cells were transfected by intranuclear microinjection and were propagated on the same petri dishes in which they were microinjected. Cells outside the microinjected area were removed by scraping with a rubber policeman. Exponentially growing cells were typsinized and washed before electroporation. Cells transfected with protein-DNA-lipid complexes were grown to approximately 70–80% confluence before transfection.

The 491 bp fragment was generated by PCR amplification from the T6/20 plasmid (Rommens et al. (1989) op.cit., incorporated herein by reference) and verified by restriction enzyme mapping and propagated as described previously. After digestion with EcoRI and HindIII, a 860 bp insert was isolated following electrophoresis in 0.8% SeaPlaque agarose gel. The 860 bp fragment contained CFTR exon 10, as well as 5' and 3' intron sequences, as defined by the restriction enzyme cleavage sites (Zielenski et al. (1991) op.cit.). A 50 ng aliquot of the fragment was amplified by PCR using primers CF1 and CF5 (Table 1) to generate a 491 bp fragment. The conditions for amplification were denaturation, 94° C. for 1 min; annealing, 53° C. for 30 sec; extension, 72° C. for 30 sec with a 4 sec/cycle increase in the extension time for 40 cycles. The fragment size was confirmed by electrophoresis on a 1% agarose gel, then amplified in bulk in 20 separate PCR amplifications, each containing 50 ng of target DNA. The 491 bp PCR products were extracted with phenol:chloroform:isoamyl alcohol (25:24:1) extraction and precipitated with ethanol. DNA precipitates were collected by centrifugation in an Eppendorf microcentrifuge and resuspended at a final concentration of 1 mg/ml. The 491 bp fragment contained exon 10 (193 bp), as well as 5' (163 bp) and 3' (135 bp) flanking intron sequences, as defined by primers CF1 and CF5.

The 491 nucleotide fragments were coated with recA protein using the reaction buffer of Cheng (Cheng, et al. (1988) *J. Biol. Chem.* 263: 15110, incorporated herein by reference). Typically, the 491 bp DNA fragment (5 μg) was denatured at 95° C. for 10 min, then added to a 63 μl of coating buffer containing 200 μg of recA protein, 4.8 mM ATPγS, and 1.7 μl reaction buffer (100 mM Tris-Ac, pH 7.5 at 37° C.; 10 mM dithiothreitol; 500 mM NaAc, 20 mM MgAc, 50 percent glycerol) and incubated for 10 min at 37° C. Next, the MgAc concentration was increased to a final concentration of about 22 mM by addition of 7 μl of 200 mM MgAc. Under these conditions, the 491 nucleotide fragment was coated with recA protein at a molar ratio of 3 bases per 1 recA molecule. After coating the fragments were immediately placed on ice at 4° C. until transfection (10 min to 1 hr).

Microinjection, when used, was performed with an Eppendorf 5242 microinjection pump fitted to an Eppendorf 5170 micromanipulator using borosilicate pipettes (Brunswick, 1.2 OD×1.9ID) fabricated into a microneedle with a Sutter Instruments (P-87) micropipette puller. The micropipettes were filled by capillary force from the opposite side of the needle. Approximately 100 pipettes were used for injecting of 4000 cells. Cells were injected with approximately 1,000–10,000 fragments per cell by intranuclear injection with 120 hPa for 0.1–0.3 s at a volume of 1–10 fl/nucleus. Microinjected cells were viewed with an Olympus IMT-2 inverted microscope during the injection. The area of the petri dish containing injected cells was marked with 2 to 5 mm diameter rings. Needle microinjection was performed in cells grown on 10 separate 60 mm petri dishes. Cells were injected at room temperature in culture medium after two washes in phosphate buffered saline (PBS). After microinjection, noninjected cells in the culture were removed by scraping. Injected cells were grown at 37° C. in a humidified incubator at 7 days and then harvested for DNA and RNA.

Electroporation experiments were performed using recA-coated 491-mer ssDNA as described above. Approximately 1×10⁸ exponentially growing cells were suspended in 400 μl of coating buffer with 5 μg of recA coated-DNA. The cell suspension was pre-incubated on ice for 10 min and electroporated at room temperature with 400 V and 400 μF in a BTX 300 electroporator (BTX Corporation, San Diego, Calif.). After electroporation, cells were incubated on ice for an additional 10 min, diluted in Eagle's minimal essential medium (MEM) supplemented with 10% fetal bovine serum (FBS) and 100 μg/ml streptomycin, 100 U/ml penicillin (Cozens et al. (1992) *Proc. Natl. Acad. Sci. (U.S.A.)* 89: 5171; Gruenert et al. (1988) *Proc. Natl. Acad. Sci. (U.S.A.)* 85: 5951; Kunzelmann, (1992) op.cit.), and then seeded in T75 flasks. Under these conditions of elecroporation, approximately 30–50% of the cells survive. Cells were cultured for 507 days at 37° C. and then harvested for DNA and RNA.

Protein DNA-lipid complexes (liposomes) were prepared. Briefly, dioleoylphosphatidylethanolamine (PtdEtn, DOPE) was used for preparing liposomes by drying 4 μM solutions of the lipid under nitrogen at room temperature. The lipid film was rehydrated with 4 ml of 30 mM Tris-HCl buffer (pH 9), then sonicated for 15 minutes under an atmosphere or argon. The protein-DNA complex was prepared in polystyrene tubes by diluting 20 μg of recA-coated 491-base DNA in 30 mM Tris-HCl, (pH 9) buffer. Protein (GmS) was also diluted with 30 mM Tris HCl (pH 9) to a final concentration of 2 mg/ml from a 20 mg/ml stock solution prepared in dimethyl sulfoxide. The protein (40 μg) was added to the DNA and rapidly mixed. Next, 175 μl of the liposome solution (175 nmoles of lipid) were added to the peptide DNA mixture.

Genomic DNA was isolated and purified from cells as described in Maniatis op.cit. to test for homologous DNA recombination. Cellular DNA was first PCR-amplified with primers CF1 and CF6 (Table 1). CF1 is within the region of homology defined at the 5' end of the 491 bp CFTR fragment CF6 is outside the region of homology at the 3' end of this fragment.

The conditions for the PCR amplification were as follows: CF1/CF6; 684/687 bp fragment; primers, 0.5 μM; DNA, 1–2 μg; denaturation; 94° C. for 1 min; annealing; 53° C. for 45 s; extension; 72° C. for 90 s with a 4-s/cycle increase in extension time for 40 cycles; $Mg^{+2}$ 1.5 mM. DNA fragments were separated by agarose electrophoresis and visualized by staining with ethidium bromide, then transferred to Gene Screen Plus filters (DuPont). The DNA was then hybridized with the allele-specific normal CFTR $^{32}$P-end-labeled DNA probe defined by oligo N as described by Cozens et al. (1992) op.cit.; Kunzelmann (1992) op.cit., incorporated herein by reference. The presence of wild-type (WT) sequences was determined autoradiographically by hybridization with the radiolabeled DNA probe.

Homologous recombination was verified in a second round of PCR DNA amplification using the 687/684 bp fragment as a DNA template for amplification. The primers used in this allele-specific reaction were CF1 and the oligo N or oligo ΔF. The size of the DNA fragments was 300 bp (oligo N) or 299 bp (oligo ΔF).

The conditions for the reaction were as follows: CF1/oligo N/ΔF; 300/299 bp fragment; primers, 0.5 μM; DNA, 1–μg; denaturation, 95° C. for 45 s; annealing, 51° C. for 30 s; extension, 72° C. for 30 s with a 3-s/cycle increase in extension time for 40 cycles; $Mg^{+2}$, 1.5 mM. In DNA from transfected ΣCFTE29o- cells, amplified with the CF1/oligo N primers, a PCR product was detected only if the wild-type CFTR sequences were present. Amplification with the CF1/oligo ΔF gives a PCR DNA product of DNA targets purified from transfected and nontransfected ΣCFTE29o- cells but not for DNA targets isolated from control normal cells (16HBE14o-). The presence of wild-type CFTR sequences in the amplified DNA fragments was also determined autoradiographically after hybridization with $^{32}$P-5'-endlabeled oligo N as probe.

Cytoplasmic RNA was isolated and denatured at 95° C. for 2 min, then reverse-transcribed using the DNA polymerase provided in a PCR RNA Gene Amp kit according to manufacturer's instructions (Perkin-Elmer/Cetus). First strand cDNA was amplified by using primer CF17 at the 5' end of exon 9 and the allele-specific oligo N or oligo ΔF primers. The length of the PCR fragments is 322 bp (CF17/oligo N) and 321 bp (CF17/oligo ΔF).

The conditions for PCR amplification are CF17/oligo N/ΔF, 322/321 bp fragment; primers, 1 μM; denaturation, 94° C. for 1 min; annealing, 51° C. for 30 s; extension, 72° C. for 20s with a 4-s/cycle increase in extension time for 40 cycles; $Mg^{+2}$, 0.8 mM. DNA fragments were visualized after electrophoresis on ethidium bromide-stained 1% agarose gels. In addition to the allele-specific PCR amplification of first-strand cDNA, Southern hybridization was performed as described above. Fragments were transferred to Gene Screen Plus filters then hybridized with allele-specific oligo N probe under the same conditions used for the Southern analysis of the genomic DNA (Kunzelmann et al. (1992) op.cit.; Cozens et al. (1992) op.cit.). The presence of wild-type CFTR RNA was confirmed by hybridization and autoradiography of RNA extracted from normal (16HBE14o-) control DNA and in DNA of transfected ΣCFTE29o-cells.

Hybridization was performed as described previously (Cozens et al. (1992) op.cit.). DNA fragments were separated by agarose gel electrophoresis. DNA was denatured with 0.4 N NaOH and 0.6 M NaCl for 30 min, then washed once with 1.5 M NaCl and 0.5 M Tris-HCl for 30 min. DNA was transferred to Gene Screen Plus membrane (NEN-DuPont) by capillary blot, again denatured with 0.4 N NaOH for 1 min, and then neutralized with 0.2 M Tris-HCl (pH 7.0). DNA on membranes was prehybridized for 1 h at 37° C. in 6 X SSC, 5 X Denhardt's solution, 1% SDS, containing 100 μg/ml of denatured salmon sperm DNA (Sigma). Oligonucleotide probes (oligo N or oligo ΔF; 10 ng) were $^{32}$P-5' -endlabeled with 20 units of T4 kinase and 40 μCi $^{32}$P-γ-ATP for 30 min at 37° C. Unincorporated nucleotides were removed by centrifugation of the reaction mix through a minispin column (Worthington Biochemical Corp., Freehold, N.J.). Hybridization was performed overnight at 37° C. Membranes were washed twice for 5 min each time in 2 x SSC at room temperature, twice for 30 min in 2 x SSC, 0.1% SDS at 45° C., and once in 0.1 x SSC for 30 min at room temperature. After washing, hybrids on membranes were analyzed autoradiographically by exposure to x-ray film.

Analysis of ΣCFTE29o- DNA shows replacement of the endogenous mutant (ΔF508) sequences with the exogenous normal fragment as evidenced by PCR amplification of genomic DNA and allele-specific Southern blot hybridization. PCR primers, one inside (CF1), and one outside (CF6) the region of homology (491 bp), were used to test whether the amplified DNA band was possibly due to amplification of any residual DNA fragment remaining in the cell after the transfection or by possible random DNA integration. A 687 bp fragment contains normal CFTR sequences while the 684 bp fragment is generated from ΔF508 CFTR DNA. To determine whether endogenous ΔF508 sequences were replaced with exogenous normal CFTR sequences, we analyzed aliquots of the 687 or 684 bp amplification fragments by Southern hybridization using $^{32}$P-end-labeled DNA probes specific for the ΔF508 or wild-type sequences (Table 1). In addition, the 687 bp fragment was PCR amplified by using the CF6 primer and a primer specific for either ΔF508 (oligo ΔF) or normal sequences (oligo N). The second round of DNA amplification with the CF1/oligo N or ΔF primer pair combination yields 300/299 bp fragments, respectively. With the CF1/oligo N primer pair combination, a fragment will be detected only if the mutant DNA has been replaced by normal sequences. Further confirmation of homologous DNA recombination was tested by allele-specific Southern blot hybridization of the 300/299 bp fragments Analysis of cytoplasmic RNA to detect normal exon 10 sequences in CFTR mRNA, verify that the homologous DNA recombination was legitimate and that normal CFTR mRNA is expressed in the cytoplasm. To test whether the PCR generated DNA fragments were exclusively CFTR mRNA-derived, primers in exon 9 (CF17) and allele-specific (normal, oligo N or ΔF508, oligo ΔF) primers in exon 10. This amplification with primers CF17/N yields a 322 bp normal fragment only if transcription of homologously recombined DNA has occurred. A 321 bp DNA fragment would be generated if the ΔF508 mutation were present. Furthermore, Southern hybridization analysis with allele-specific $^{32}$P-end-labeled probes differentiated between normal and ΔF508 mutant sequences and were also used to confirm expression of wild-type CFTR mRNA in the cytoplasm.

Homologous recombination between the targeting polynucleotide comprising WT CFTR DNA and ΔF508 mutant cellular DNA allelic targets was evaluated by analysis of cellular DNA and RNA isolated from transfected and nontransfected ΣCFTE29o-cell cultures. Nuclear genomic DNA and cytoplasmic RNA were isolated 6 days after transfection, CFTR exon 1 sequences were amplified by PCR. Oligonucleotide primers (Table 1) were used to amplify the region of CFTR DNA spanning exon 10. One PCR primer (CF 1) was within the region of homology defined by the 491 bp DNA fragment (sense primer), and the other (CF 6) was outside the homologous region in the 3' intron (antisense primer). This DNA amplification reaction produces a 687 bp fragment with normal human CFTR DNA or a 684 bp fragment if the DNA contains the ΔF508 mutation, as shown in FIG. 10A. Southern hybridization was carried out on the 687/684 bp DNA fragments generated from amplification of genomic DNA from cell cultures by microinjection or by transfection with the protein-DNA-lipid complex, shown in FIG. 10B. A probe consisting of $^{32}$P-end-labeled oligonucleotide DNA that hybridized only to DNA sequences generated from a normal exon 10 was used. DNA from all microinjected and transfected cells produced specific hybrids as evidenced by autoradiographic hybridization. For cells microinjected with the 491 nucleotide fragment (FIG. 10B, lane 2), the present of normal exon 10 sequences indicated homologous replacement at at least a frequency of $\geq 2.5 \times 10^{-4}$. This result indicates at least one correctly targeted homologous DNA replacement in about 4000 microinjected nuclei. Other similar experiments using either electroporation or protein-DNA-lipid transfection to transfer the recA-coated 491 nucleotide CFTR DNA fragments also showed homologous recombination with the normal CFTR sequence in transfected CF cells. No hybridization was observed in control nontransfected (or mock-injected ΣCFTE29o- cells). In each cell transfected with normal CFTR DNA, analysis of the genomic DNA in a second round of allele-specific amplification of the 687/684 bp fragments with primers CF1/oligo N (Table 1) clearly showed the 300 bp fragment expected when wild-type CFTR sequences are present, as shown in FIG. 11A. Fragments were detected for control 16HBE14o- cells (FIG. 11A, lane 2) and cells transfected with recA-coated DNA (FIG. 11A, lanes 5 and 6). A 299 bp fragment (ΔF508-specific primer ends one base closer to the CF1 than the oligo N) was detected in DNA from nontransfected ΣCFTE29o- cells amplified with CF1/oligo ΔF primers (FIG. 11A, lane 4). No fragment was detected in DNA from nontransfected ΣCFTE29o- cells reamplified with the CF1/ oligo N primers (FIG. 11A, lane 3). Allele-specific Southern blot hybridization of these fragments with the $^{32}$P-endlabeled oligo N probe resulted in autoradiographic hybridization signals from control normal and transfected CF cells (FIG. 11B, lanes 1, 4, and 5) but not from DNA of nontransfected CF cells amplified with CF1 and oligo-N or -ΔF (FIG. 11B lanes 2 and 3). We tested whether any residual 491 nucleotide DNA fragments which might remain in the cell after 6 days could act as a primer for the PCR reaction, genomic ΣCFTE29o- DNA was incubated with an equivalent number of recA-coated DNA fragments ($10^3$–$10^4$) introduced by microinjection (FIG. 12). One antisense primer contains the wild-type normal (N) sequence while the other contains the ΔF508 (ΔF) mutation. Amplification with the CF1/ΔF primer combination gives a 299 bp fragments when the ΔF508 mutation is present. No DNA fragment product was detected when the CF1/N primer combination was used with control nontransfected ΣCFTE29o- DNA (FIG. 12, lane 2). However, when the CF1/ΔF primer combination was used for DNA amplification in nontransfected ΣCFTE29o- cells, a DNA product of the expected size (299 bp) was produced (FIG. 12, lane 1). These results indicate that all residual 491 nucleotide DNA fragments which might remain in the cells after 6 days of culture were incapable of competing with the CF1 PCR primers in the PCR amplification of the 687/684 bp fragments.

TABLE 1

PCR Primers and Oligonucleotides

| Oligo-nucleotide | DNA Strand | DNA Sequence |
|---|---|---|
| CF1 | S | 5'-GCAGAGTACCTGAAACAGGA |
| CF5 | A | 5'-CATTCACAGTAGCTTACCCA |
| CF6 | A | 5'-CCACATATCACTATATGCATGC |
| CF17 | S | 5'-GAGGGATTTGGGGAATTATTTG |
| OLIGO N | A | 5'-CACCAAAGATGATATTTTC |
| OLIGO AF | A | 5'-AACACCAATGATATTTTCTT |

Notes:
(1) CF1 and CF5 PCR primers were used to synthesize the 491 bp fragment used for the targeting polynucleotide.
(2) CF1 and CF6 PCR primers were used to amplify the 687/684 bp CFTR fragment.
(3) The CF17 primer is located at the 5' end of exon 9 and was used for amplification of first strand cDNA derived from CFTR mRNA.
(4) Oligo N and Oligo AF are allele-specific probes and can also be used as allele-specific PCR primers for amplifying the 300/299 bp fragments (DNA analysis) and the 322/321 bp fragments (RNA analysis).
(5) Sense (S) and antisense (A) primers are designated under DNA Strand and indicate the sense of the strand relative to the transcribed direction (i.e., the CFTR mRNA).

The corrected CFTR DNA must also be expressed at the mRNA level for normal function to be restored. Therefore cytoplasmic CFTR mRNA was analyzed for the presence of a normal CFTR RNA sequence in the ΔF508 region of exon 10. Cytoplasmic RNA was isolated from the cells, reverse-transcribed with DNA polymerase and PCR-amplified as first-strand cDNA. This amplification was performed with a PCR primer located in exon 9 (CF17, sense) and CFTR allele-specific PCR primer in exon 10 (oligo N or ΔF, antisense). The exon 10 primer contains the CF mutation site, and the resulting fragment is 322 bp in normal DNA or 321 bp in DNA containing the ΔF508 mutation. Amplification of genomic DNA is eliminated by using primers that require amplification across intron/exon boundaries. Amplified cDNA generated from normal control 16HBE140- cells and experimentally transfected cells yielded DNA product fragments with the CF17/oligo N, whereas nontransfected ΣCFTE29o- cells only showed a DNA fragment after amplification with the CF17/oligo ΔF primers but not with the CF17/oligo N primers. Cells electroporated with wild-type 491-mer CFTR DNA showed the presence of wild-type CFTR mRNA. In addition, protein-DNA-lipid-transfected ΣCFTE29o- cell cultures also showed the presence of wild-type CFTR mRNA in cells transfected with the recA-coated 491 nucleotide fragment. Southern hybridization of the 322/321 bp cDNA fragments with the $^{32}$P-end-labeled N oligonucleotide DNA probe showed the specificity of the PCR amplification and produced specific autoradiographic hybridization signals from all cell cultures transfected with recA-coated 491 nucleotide targeting polynucleotide. No autoradiographic hybridization signals were detected in non-transfected ΣCFTE29o- cells amplified with the CF17/oligo N or oligo ΔF primers. These analyses verify that the genomic DNA homologously recombined with the WT 491-mer DNA at the ΔF508 CFTR DNA locus resulting in RNA expressed and transported to the cytoplasm as wild-type CFTR mRNA.

This evidence demonstrates that human CFΔF508 epithelial cells CFTR DNA can homologously recombine with targeting polynucleotides comprising small fragments of WT CFTR DNA resulting in a corrected genomic CFTR allele, and that a recA-coated targeting polynucleotide can be used in transfection reactions in cultured human cells, and that cystic fibrosis ΔF508 mutations can be corrected in genome DNA resulting in the production of normal CFTR cytoplasmic mRNA.

Taken together, the data provided indicates that small (e.g., 491-mer) ssDNA fragments can find their genomic homologues when coated with recA protein and efficiently produce homologously targeted intact mammalian cells having a corrected gene sequence. Analysis of CFTR in cytoplasmic RNA and genomic DNA by allele-specific polymerase chain reaction (PCR) amplification and Southern hybridization indicated wild-type CFTR DNA sequences were introduced at the appropriate nuclear genomic DNA locus and was expressed as CFTR mRNA in transfected cell cultures. Thus, in human CF airway epithelial cells, 491 nucleotide cytoplasmic DNA fragments can target and replace the homologous region of CFTR DNA containing a 3 bp ΔF508 deletion.

Correctly targeted homologous recombination was detected in one out of one microinjection experiment with recA-coated targeting polynucleotide, two of two different electroporation experiments with recA-coated targeting polynucleotide, and one of one lipid-DNA-protein complex transfection experiment with recA-coated targeting polynucleotide. Taken together, these 4 separate experiments strongly indicate that homologous recombination with relatively small recA-coated targeting polynucleotides (491-mer CFTR DNA) is feasible for treatment of human genetic diseases, and can be performed successfully by using various methods for delivering the targeting polynucleotide-recombinase complex.

Although the present invention has been described in some detail by way of illustration for purposes of clarity of understanding, it will be apparent that certain changes and modifications may be practiced within the scope of the claims.

What is claimed is:

1. A method for targeting and altering, by homologous recombination, a preselected target DNA sequence in a eukaryotic cell in vitro to make a targeted sequence modification, said method comprising:

introducing into at least one eukaryotic cell at least one recombinase and at least two single-stranded targeting polynucleotides which are substantially complementary to each other, and which further comprise a homology clamp that substantially corresponds to or is substantially complementary to said preselected target DNA sequence and;

identifying a eukaryotic cell having a the at a preselected target DNA sequence.

2. A method according to claim 1, wherein said recombinase is a recA recombinase.

3. A method according to claim 2, wherein said recA recombinase is E. coli recA recombinase.

4. A method according to claim 1, wherein at least one of said targeting polynucleotides is conjugated by non-covalent binding to a cell-uptake component.

5. A method according to claim 4, wherein said cell-uptake component is conjugated to said at least one targeting polynucleotides by noncovalent binding to a poly-L-lysine conjugate or a cationic lipid.

6. A method according to claim 4, wherein the cell-uptake component comprises poly-L-lysine conjugated to an asialoglycoprotein.

7. A method according to claim 4, wherein said at least one targeting polynucleotides is non-covalently conjugated to a cell-uptake component and to a recombinase, forming a cell targeting complex.

8. A method according to claim 1, wherein said targeting polynucleotides form a double-stranded nucleic acid.

9. A method according to claim 1, wherein the targeted sequence modification comprises a deletion of at least one nucleotide from said preselected target DNA sequence in said eukaryotic cell.

10. A method according to claim 1, wherein the targeted sequence modification comprises the addition of at least one nucleotide to said preselected target DNA sequence in said eukaryotic cell.

11. A method according to claim 1, wherein the recombinase and said targeting polynucleotides are introduced into the eukaryotic cell simultaneously.

12. A method according to claim 11, wherein the recombinase and the targeting polynucleotides are introduced into the eukaryotic cell by microinjection, electroporation, and contacting the cell with a lipid-protein-targeting polynucleotide complex that facilitates entry into said eukaryotic cell.

13. A method according to claim 1, wherein said identifying of the targeted cell is accomplished by detection of the targeted DNA sequence modification by Southern blot, PCR detection, or phenotype selection.

14. A method according to claim 13, wherein said phenotype selection comprises selection for cells expressing a neo or HSV-tk drug-resistance gene.

15. A method according to claim 1, wherein the targeted sequence modification comprises the substitution of at least one nucleotide for at least one nucleotide in said preselected target DNA sequence in said eukaryotic cell.

16. A method for generating a targeted sequence modification in a preselected endogenous target DNA sequence in a eukaryotic cell in vitro, comprising:

introducing into a eukaryotic cell, a recombinase having strand transfer activity and at least two single-stranded targeting polynucleotides which are substantially complementary to each other, and which further comprise a homology clamp that substantially corresponds to or is substantially complementary to said preselected endogenous target DNA sequence; and identifying a eukaryotic cell having the targeted sequence modification at said preselected endogenous target DNA sequence.

17. A method according to claim 16, wherein said identifying of the targeted cell is accomplished by detection of the targeted DNA sequence modification by Southern blot, PCR detection or phenotype selection.

18. A method according to claim 17, wherein said phenotype selection comprises selection for cells expressing a neo or HSV-tk drug-resistance gene.

19. A method according to claim 16, wherein the recombinase having strand transfer activity is selected from the group consisting of: recA, recA803, uvsX, and rec1.

20. A method for targeting and altering, by homologous recombination, a preselected DNA sequence in a eukaryotic cell in vitro to make a targeted sequence modification, said method comprising introducing into at least one eukaryotic cell at least one recA recombinase and at least two single-stranded targeting polynucleotides which are substantially complementary to each other, and which further comprise a homology clamp that substantially corresponds to or is substantially complementary to a preselected target DNA sequence; and identifying a eukaryotic cell having the targetet DNA sequence modification at a preselected target DNA sequence.

* * * * *

UNITED STATES PATENT AND TRADEMARK OFFICE
CERTIFICATE OF CORRECTION

PATENT NO.     : 6,255,113 B1
DATED          : July 3, 2001
INVENTOR(S)    : Zarling et al.

It is certified that error appears in the above-identified patent and that said Letters Patent is hereby corrected as shown below:

Column 3,
Line 39, the phrase "charactiersistics" should read -- characteristics --.
Lines 43 and 45, for the word "compunds", each occurrence, should read -- compounds --.

Column 5,
Line 13, the word "catalzye" should read -- catalyze --.

Column 7,
Line 20, the phrase "associa-" should read -- associ --.

Column 11,
Line 62, the word "associted" should read -- associated --.

Column 13,
Line 50, the phrase "is is" should read -- is --.

Column 18,
Line 48, the word "conplexes" should read -- complexes --.

Column 20,
Line 21, the word "poynucleotide" should read -- polynucleotide --.

Column 22,
Lines 15-16, the word "subtiutents" should read -- substituents --.
Lines 30-31, the word "polynuclotides" should read -- polynucleotides --.
Line 50, the word "chromososomal" should read -- chromosomal --.

Column 23,
Line 36, the word "dithithreitol" should read -- dithiothreitol --.

Column 26,
Line 17, the word "supressor" should read -- supperssor --.

Column 28,
Line 57, the phrase "SCi." should read -- Sci. --.

Column 29,
Line 48, the word "typsinized" should read -- trypsinized --.

UNITED STATES PATENT AND TRADEMARK OFFICE
CERTIFICATE OF CORRECTION

PATENT NO. : 6,255,113 B1
DATED : July 3, 2001
INVENTOR(S) : Zarling et al.

It is certified that error appears in the above-identified patent and that said Letters Patent is hereby corrected as shown below:

Column 30,
Line 61, the word "elecroporation" should read -- electroporation --.

Column 33,
Line 37, the phrase "at at" should read -- at --.

Column 36,
Line 5, the phrase "DNA sequence and;" should read -- DNA sequence; and --.
Line 6, the phrase "a the" should read -- the targeted DNA sequence modification --.
Line 39, cancel beginning with "12. A method according to claim 11," to and including "said eukaryotic cell."
Line 43, insert the following claim:

-- 12. A method according to claim 11, wherein the recombinase and the targeting polynucleotides are introduced into the eukaryotic cell by microinjecting, electroporating, or contacting the cell with a lipid-protein-targeting polynucleotide complex that facilitates entry into said eukaryotic cell. --

Column 38,
Line 9, the word "targetet" should read -- targeted --.

Signed and Sealed this

Second Day of December, 2003

JAMES E. ROGAN
*Director of the United States Patent and Trademark Office*